(12) United States Patent
Tilson et al.

(10) Patent No.: US 12,059,534 B2
(45) Date of Patent: Aug. 13, 2024

(54) INFLATABLE MEDICAL BALLOONS WITH CONTINUOUS FIBER WIND

(71) Applicant: LOMA VISTA MEDICAL, INC, Tempe, AZ (US)

(72) Inventors: Alexander Quillin Tilson, Burlingame, CA (US); Jonathan Kurniawan, Belmont, CA (US); Mark Christopher Scheeff, Oakland, CA (US)

(73) Assignee: LOMA VISTA MEDICAL, INC., Tempe, AZ (US)

( * ) Notice: Subject to any disclaimer, the term of this patent is extended or adjusted under 35 U.S.C. 154(b) by 93 days.

(21) Appl. No.: 17/723,754

(22) Filed: Apr. 19, 2022

(65) Prior Publication Data

US 2022/0233811 A1 Jul. 28, 2022

Related U.S. Application Data

(63) Continuation of application No. 16/601,652, filed on Oct. 15, 2019, now Pat. No. 11,351,338, which is a continuation of application No. 14/787,038, filed as application No. PCT/US2014/035293 on Apr. 24, 2014, now Pat. No. 10,485,949.

(Continued)

(51) Int. Cl.
*A61M 25/10* (2013.01)
*A61M 25/00* (2006.01)

(52) U.S. Cl.
CPC ...... *A61M 25/005* (2013.01); *A61M 25/1027* (2013.01); *A61M 25/104* (2013.01); *A61M 2025/1084* (2013.01); *A61M 2025/1093* (2013.01)

(58) Field of Classification Search
CPC ............ A61M 25/005; A61M 25/1027; A61M 25/104; A61M 25/0051–0054; A61M 25/10; A61M 25/0067; A61M 25/0069; A61M 25/007; A61M 25/0071; A61M 2025/1093; A61M 2025/1084; A61M 2025/0056–0059; A61M 2025/0062; A61M 2025/0064; A61M 2025/0065
See application file for complete search history.

(56) References Cited

U.S. PATENT DOCUMENTS

2005/0271844 A1 12/2005 Mapes
2006/0085024 A1* 4/2006 Pepper ................. A61L 29/085
428/35.9

(Continued)

*Primary Examiner* — Erich G Herbermann
(74) *Attorney, Agent, or Firm* — Andrew D. Dorisio; Dickinson Wright PLLC

(57) ABSTRACT

A fiber-reinforced is medical balloon includes a cylindrical central portion. The balloon includes first and second conical portions connected to the cylindrical central portion along a central longitudinal axis extending from a first end of the balloon to a second end of the balloon. The balloon includes a plurality of first fiber strands extending from the first end of the balloon to the second end of the balloon. Each strand of the plurality of first fiber strands runs substantially parallel to the longitudinal axis through the cylindrical central portion and radially around at least a portion of the first and second conical portions. The balloon includes at least one second fiber strand extending radially around the central portion. The strands are applied as part of a single continuous fiber.

16 Claims, 21 Drawing Sheets

Related U.S. Application Data

(60) Provisional application No. 61/815,689, filed on Apr. 24, 2013.

(56) References Cited

U.S. PATENT DOCUMENTS

2008/0033477 A1* 2/2008 Campbell .......... A61M 25/104
                                                606/194
2021/0001094 A1* 1/2021 Hall .................. A61M 25/10

* cited by examiner

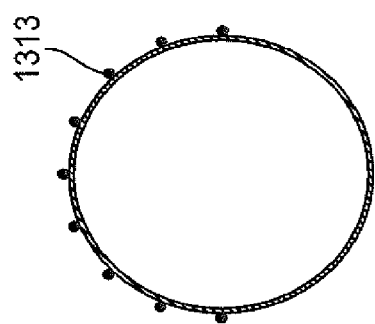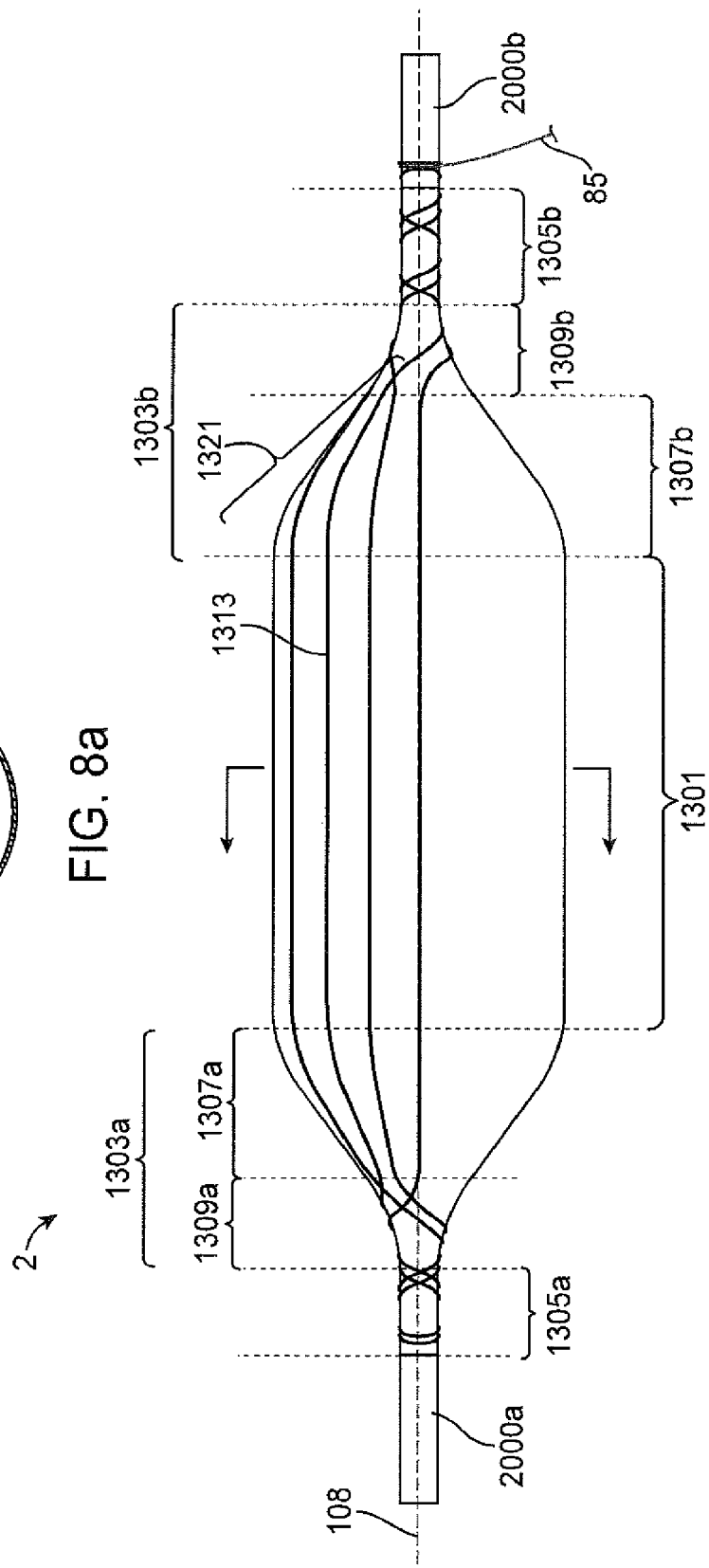

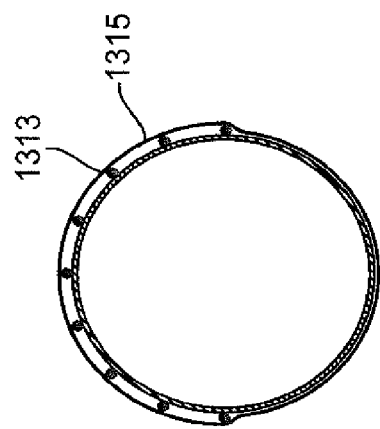
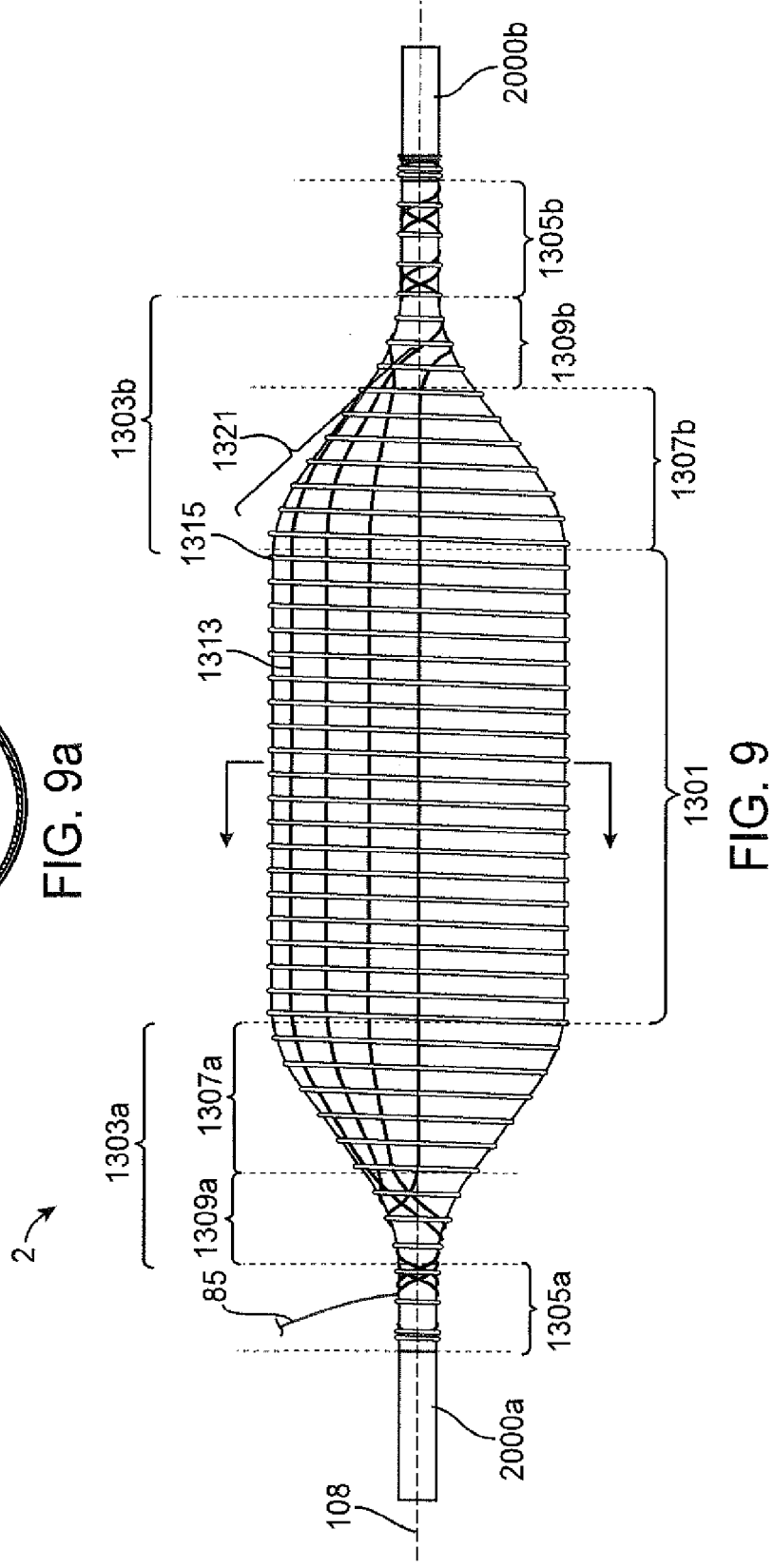
FIG. 9a
FIG. 9

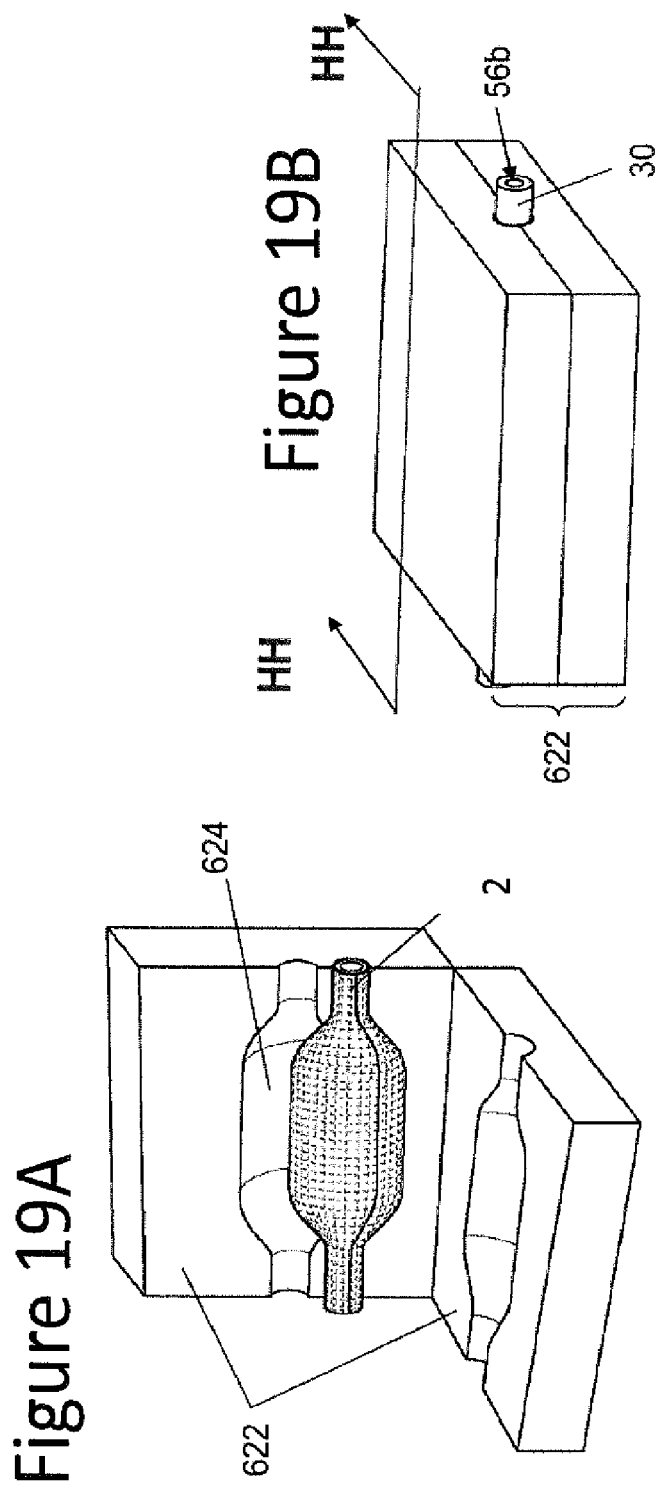

:
INFLATABLE MEDICAL BALLOONS WITH CONTINUOUS FIBER WIND

INCORPORATION BY REFERENCE

All publications and patent applications mentioned in this specification are herein incorporated by reference to the same extent as if each individual publication or patent application was specifically and individually indicated to be incorporated by reference. This application also incorporates herein by reference U.S. Provisional Patent Application Ser. No. 61/815,689 and U.S. Provisional Patent Application Ser. No. 61/656,404.

BACKGROUND

Fiber based devices and expandable devices, such as balloons, are widely used in medical procedures. In the case of a balloon, it is inserted, typically on the end of a catheter, until the balloon reaches the area of interest. Adding pressure to the balloon causes the balloon to inflate. In one variation of use, the balloon creates a space inside the body when the balloon inflates.

Balloons may be used in the heart valves, including during Balloon Aortic Valvuloplasty (BAV) and Transcatheter Aortic Valve Implantation (TAVI). The balloons can be used to open a stenosed aortic valve. A stenosed valve may have hard calcific lesions which may tend to tear or puncture a balloon. Additionally, a precise inflated balloon diameter may be desired for increased safety and control.

Balloons may be used to move plaque away from the center of a vascular lumen toward the vasculature walls, such as during an angioplasty or a peripheral vasculature procedure. During this procedure, a balloon tipped catheter is placed in a vascular obstruction. As the balloon is inflated, the vessel constriction is dilated, resulting in improved blood flow.

Two basic types of balloons are utilized: One is a high pressure, low-compliance balloon. The other is a lower pressure, high-compliance balloon.

High-compliance medical balloons are often composed of urethane, latex, silicone, PVC, Pebax, and other elastomers. As the pressure in a high-compliant balloon is increased, the balloon dimensions expand. Once the pressure is reduced, the high-compliance medical balloon may return to its original shape, or near its original shape. High-compliance medical balloons can easily expand several times in volume between zero inflation pressure and burst.

Traditional high-compliance medical balloons can be inadequate for many reasons. High-compliance, or highly elastic medical balloons typically cannot reach high pressures because their walls have a low tensile strength and their walls thin out as the balloon expands. In some instances, high-compliance medical balloons provide insufficient force to complete a procedure. Exceeding the rated pressure of a high-compliance medical balloon creates an excessive risk of balloon failure which can lead to serious complications for the patient. Moreover, high-compliance medical balloons also have poor shape control. As a high-compliance medical balloon expands, it may assume a shape dictated mostly by the particulars of the environment inside the patient rather than the clinical goals. In some cases, this can be contrary to what the medical practitioner desires. Many medical procedures are predicated on forming a particular balloon shape reliably. Further, high-compliance medical balloons often suffer from poor puncture and tear resistance.

Low-compliance, high pressure medical balloons substantially retain their shape under comparatively high pressures. PET (polyethylene terephthalate) is the most common material for use in high pressure low-compliance balloons. PET is commonly used for high-performance angioplasty balloons. PET is stronger than other polymers, can be molded into a variety of shapes and can be made very thin (e.g., 5 µm to 50 µm (0.0002 in. to 0.002 in.)), thus giving these balloons a low profile. However, balloons made from PET walls are fragile and prone to tears. When pressed against a hard or sharp surface in the body, such as stenosis, PET balloons have poor puncture resistance. PET is very stiff so balloons made from PET may be difficult to pack or fold into a small diameter and may have poor trackability (i.e., the ability to slide and bend over a guidewire deployed through a tortuous vessel). Further, balloons made from PET, while stronger than most other balloons made from homogenous polymers, may still not be strong enough to hold pressures sufficient to complete certain medical procedures. Additionally, with a large balloon diameter (For example, 20 mm or greater), a PET balloon still has excessive compliance for procedures such as BAV and TAVI. Nylon balloons are an alternative material for low-compliance, high pressure balloons. However, these nylon balloons are typically weaker than PET balloons and so can contain less pressure. Nylon readily absorbs water, which can have an adverse effect on Nylon's material properties in some circumstances. Nylon has improved puncture resistance over PET and is more flexible than PET.

Fiber-reinforced composite balloons are another alternative low-compliance, high pressure medical balloon. Such fiber-reinforced composite balloons can advantageously sustain high pressures, provided precise shape control, and are highly resistant to tear and puncture. The manufacturing process for fiber-reinforced balloons, however, can be complicated and expensive, requiring the application of multiple different layers of fibers in order to achieve the desired support. Often, at least one of these layers consists of a fabric de-convolution pattern layer wrapped around a base balloon. Such forming and wrapping of the fabric pattern layer can be cumbersome, labor and equipment intensive, and time consuming. Further, depending upon the orientation of the fibers, the tear pattern of a fiber-reinforced balloon (sometimes referred to as its "rip" or "rip-stop" properties) upon bursting can result in enhanced difficulties in removing the balloon through a shaft.

Thus, there exists the need to create a fiber-reinforced device, such as a balloon, that can be manufactured quickly and easily while still maintaining its ability to withstand high pressures, provide precise shape control, and have highly controlled tear properties.

SUMMARY OF THE DISCLOSURE

In general, in one embodiment, a medical apparatus comprises a device including a single continuous fiber extending both radially and longitudinally. In one example, the device may be a balloon including a central portion and first and second tapered portions connected to the central portion along a longitudinal axis extending from a first end of the balloon to a second end of the balloon. The single continuous fiber may extend substantially parallel to the longitudinal axis along the central portion and radially around at least a portion of at least one of the first and second tapered portions of the device.

The apparatus may further include a second fiber extending radially around the central portion of the balloon. The second fiber may be part of the single continuous fiber, which may comprise a plurality of first fiber strands. Each strand of the plurality of first fiber strands may extend at an angle of approximately 35-90 degrees relative to the longitudinal axis of the balloon as the strands extend radially around at least a portion of the first and second tapered portions. Each strand of the plurality of first fiber strands may transition from extending radially around at least a portion of the tapered portions to extending substantially parallel with the longitudinal axis in the first and second tapered portions.

The second fiber may extend at an angle of approximately 80 to 90 degrees relative to the longitudinal axis of the balloon as the second fiber extends radially around the central portion. The second fiber may extend around the first and second tapered portions at a lower pitch than a pitch of the second fiber strand around the central portion. The second fiber may extend over the first fiber, and may be over a first portion of the first fiber and under a second portion of the first fiber. The first portion of the first fiber may be on a first half of the balloon and the second portion of the first fiber is on a second half of the balloon.

A third fiber may also be provided. The third fiber may start in the first tapered portion at a location separated from the first end of the balloon. The third fiber may be part of the single continuous first fiber.

The single continuous fiber may extend radially around both the first and second tapered portions of the balloon.

In other embodiments, a fiber-reinforced medical balloon includes a cylindrical central portion. The balloon includes first and second conical portions connected to the cylindrical central portion along a central longitudinal axis extending from a first end of the balloon to a second end of the balloon. The balloon includes a plurality of first fiber strands extending from the first end of the balloon to the second end of the balloon. Each strand of the plurality of first fiber strands runs substantially parallel to the longitudinal axis through the cylindrical central portion and radially around at least a portion of the first and second conical portions. The balloon includes at least one second fiber strand extending radially around the central portion.

This and other embodiments can include one or more of the following features. The strands of the plurality of first fiber strands can be all part of a single continuous fiber. The plurality of first fiber strands and the at least one second fiber strand can be all part of a single continuous fiber. Each strand of the plurality of first fiber strands can extend at an angle of approximately 35-90 degrees relative to the longitudinal axis of the balloon as the strands extend radially around at least a portion of the first and second conical portions. Each strand of the plurality of first fiber strands can transition from extending radially around at least a portion of the conical portions to extending substantially parallel with the longitudinal axis in the first and second conical portions. The at least one second fiber strand can extend at an angle of approximately 80 to 90 degrees relative to the longitudinal axis of the balloon as the strand extends radially around the central portion. The at least one second fiber strand can extend around the first and second conical portions at a lower pitch than a pitch of the at least one second fiber strand around the central portion. The at least one second strand can extend over all of the strands of the plurality of first fiber strands. The at least one second strand can extend over a first portion of the plurality of first fiber strands and under a second portion of the plurality of first fiber strands. The first portion of the plurality of first fibers can be on a first half of the balloon and the second portion of the plurality of first fibers can be on a second half of the balloon. The fiber-reinforced medical balloon can further include a plurality of third fiber strands, the plurality of third fiber strands can start in the first conical portion at a location separated from the first end of the balloon. At least a portion of the first fiber strands and the third fiber strands may be part of a single continuous fiber.

This disclosure also pertains to a medical apparatus in the form of a balloon including a central portion and first and second tapered portions connected to the central portion. The balloon includes a longitudinal axis extending from a first end of the balloon to a second end of the balloon. A non-woven fiber layer includes a first fiber extending substantially parallel to the longitudinal axis along the central portion and a second fiber extending radially around the first tapered portion. The first fiber and the second fiber may form part of a single continuous fiber.

In general, in one embodiment, a method of making a fiber-reinforced composite balloon having a cylindrical central portion and first and second tapered portions connected to the cylindrical central portion along a central longitudinal axis extending from the first end of the balloon to the second end of the balloon is described. The method includes applying a single continuous fiber to the cylindrical central portion extending substantially parallel to the longitudinal axis of the balloon, and applying the single continuous fiber to at least one of the first and second tapered portions. The applying step may include applying the single continuous fiber radially around at least a portion of at least one of the first and second tapered portions. The method may further include applying a second fiber extending radially around the central portion of the balloon.

In another embodiment disclosed, a method of making a fiber-reinforced composite balloon having a cylindrical central portion and first and second conical portions connected to the cylindrical central portion along a central longitudinal axis extending from the first end of the balloon to the second end of the balloon, includes applying a single continuous fiber to a base layer having the cylindrical central portion and first and second conical portions to form a plurality of first fiber strands extending substantially parallel to the longitudinal axis of the balloon within the cylindrical central portion.

This and other embodiments can include one or more of the following features. Applying a single continuous fiber can include forming a fiber strand of the plurality of first fiber strands by wrapping the fiber radially around the first conical portion, laying the fiber substantially parallel to the longitudinal axis within the cylindrical central portion, and wrapping the fiber radially around the second conical portion from the first end of the balloon to the second end of the balloon. Applying a single continuous fiber can further include forming another fiber strand of the plurality of first fiber strands by changing the direction of applying the fiber so as to wrap the fiber radially around the second conical portion, laying the fiber substantially parallel to the longitudinal axis within the cylindrical central portion, and wrapping the fiber radially around the first conical portion from the second end of the balloon to the first end of the balloon. The method can further include wrapping the fiber radially around the cylindrical central portion to form at least one second fiber strand. Wrapping the fiber radially around the cylindrical central portion to form at least one second fiber strand can include wrapping the fiber radially around the cylindrical portion over at least a portion of the strands of the plurality of first strands. The method can further include wrapping a second portion of the plurality of first fiber strands over the at least one second fiber strand. Applying a single continuous fiber can include dipping the fiber in a solvated thermally weldable material to adhere the fiber to a bladder extending over the base mandrel. The method can further include cutting off the first or second end of the balloon after applying the single continuous fiber.

The disclosure may be considered to pertain to a medical apparatus, comprising a device, such as a medical tube, including a single continuous fiber applied longitudinally and radially to different portions of the device. A related method of forming a fiber-based device comprises applying a single continuous fiber longitudinally and radially to different portions of the device. The disclosure also pertains broadly to a method of forming a fiber-based device by applying a single continuous fiber longitudinally to a central portion of the device and radially to another portion of the device.

The disclosure may also pertain to a medical apparatus, comprising a balloon having a longitudinal axis, the balloon including a single fiber layer including one or more fibers extending substantially parallel to the longitudinal axis in one portion of the layer and substantially in a direction transverse to the longitudinal axis. In one embodiment, the balloon comprises a generally cylindrical portion along which fiber extends in alignment with the longitudinal axis and a generally tapered portion connected to the cylindrical portion, wherein fiber extends in a radial direction along the tapered portion. The fiber may be a single continuous fiber.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 8 shows an inflatable device having longitudinal fiber strands laid over half of the inflatable device.

FIG. 8a is a cross-section of FIG. 8.

FIG. 9 shows a hoop strand wrapped around the device of FIG. 8.

FIG. 9a is a cross-section of FIG. 9.

FIGS. 19A-B show an exemplary method for consolidating the layers or sections of an inflatable device.

DETAILED DESCRIPTION

In general, described herein is a fiber-reinforced device, such as a medical balloon, that is formed by the application of a continuous fiber wind. The balloon includes fiber or fiber strands extending substantially parallel to the longitudinal axis within the central portion and radially around the end portions of the balloon.

Figure 1:
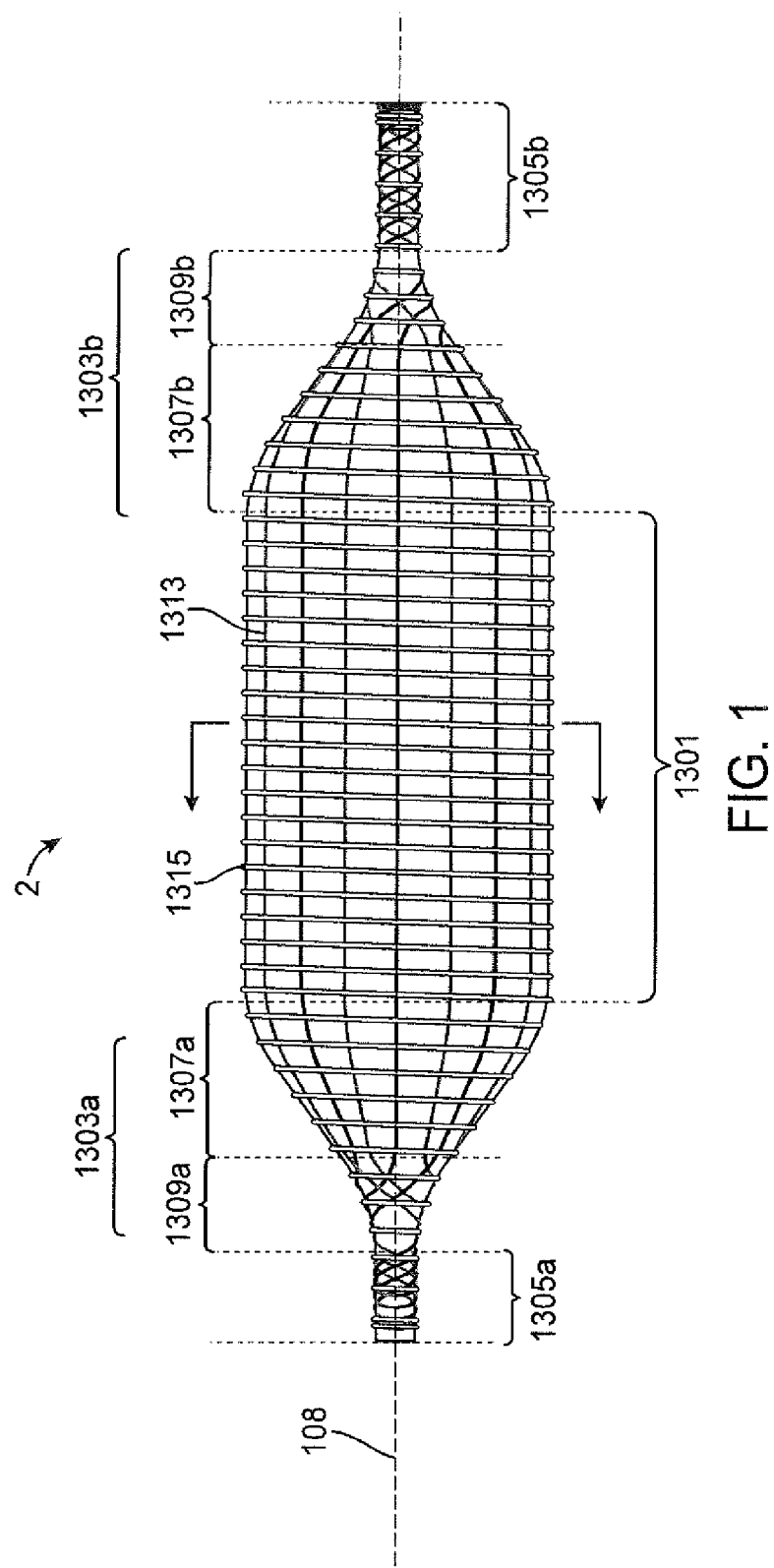
FIG. 1 shows an inflatable device having longitudinal fiber strands and a hoop fiber strand. The longitudinal fiber strands extend substantially parallel to the longitudinal axis within the central portion and radially around the end portions of the balloon. The hoop fiber strand extends radially around the inflatable device along the length of the device.

Referring to FIG. 1, an inflatable device 2 (e.g., balloon) can include a central portion 1301, tapered or conical portions 1303a,b, and end portions 1305a,b. The central portion 1301 and end portions 1305a,b can be, for example, cylindrical in shape with a substantially constant diameter across the length of the respective portions 1301, 1305a,b. In other embodiments, either the central portion 1301 or the end portions 1305a,b can vary in diameter along the length of the respective portions, such as have a slightly necked configuration. Portions 1305a,b can be reduced in length or eliminated in some embodiments. The fiber strands can also be longitudinal in end portions 1305a, b, but are illustrated as being radial.

The conical portions 1303a,b extending between the central portion 1301 and the end portions 1305a,b can have a cross-section of decreasing radius extending from the central portion 1301 to the end portions 1305a,b, i.e., can be in the shape of a cone. In some embodiments, the conical portions 1303a,b can have areas of extension or distension, such as have a bulbous or rounded section therein. Further, the conical portions 1303a,b can each have subsections 1307a,b and 1309a,b. Subsections 1307a, b can extend from the central portion 1301 and can have a substantially convex outer surface while the subsections 1309a,b can extend from the end portions 1305a,b and can have a substantially concave outer surface. The respective convex and concave outer surfaces can advantageously provide for a smooth outer surface of the balloon, even at locations of quickly changing diameter.

As is further shown in FIG. 1, the inflatable device 2 may include longitudinal fiber strands 1313 traversing the length of the inflatable device 2 from one end of the device to the other. Each longitudinal fiber strand 1313 can extend radially around the balloon at the ends of the balloon (e.g., in the end portions 1305a,b or conical portions 1303a,b). Hence, the strand 1313 may be considered to form a fiber layer of the inflatable device 2, in which fiber within the layer extends both in a direction generally parallel to the longitudinal axis (such as along the cylindrical section) and in a direction generally transverse to the longitudinal axis (such as along the end portion or portions 1305a, h). The fiber strands 1313 can thus spiral or extend helically around the ends of the inflatable device 2 at an angle of approximately 25-90 degrees relative to the longitudinal axis 108 of the balloon, such as 50-80 degrees, such as approximately 35 degrees, 40 degrees, 45 degrees, 50 degrees, 55 degrees, 60 degrees, 65 degrees 70 degrees or 75 degrees. Each fiber strand 1313 can further extend substantially parallel (e.g. ±5°, ±2°, ±1°, or ±0.1°) to the longitudinal axis 108 within the central portion 1301. For example, each fiber strand 1313 can extend substantially parallel to the longitudinal axis 108 along the entire central portion 1301.

Referring still to FIG. 1, the inflatable device 2 can further include at least one hoop fiber strand 1315. The hoop fiber strand 1315 can wind radially around at least the central portion 1301. The hoop fiber strand 1315 can extend at an angle of nearly 90 degrees relative to the longitudinal axis 108, such as 80 to 90 degrees, and can extend at least the length of the entire central portion 1301. In some embodiments, the hoop fiber strand 1315 can extend through all or part of the conical sections 1303a,b and/or the end portions 1305a,b. Further, in embodiments where the hoop fiber strand 1315 extends through all or part of the conical sections 1303a,b and/or the end portions 1305a,b, the pitch of the fiber wind can be higher (e.g. there can be more winds per inch) in the central portion 1301 than the pitch of the fiber wind towards the ends of the inflatable device 2. Advantageously, because the longitudinal fiber strands 1313 are radially wound around at least sections of the conical portions 1303a,b and provide radial support, the hoop fiber strands 1315 need not extend fully over those sections (or at as high of a pitch).

Figure 2:
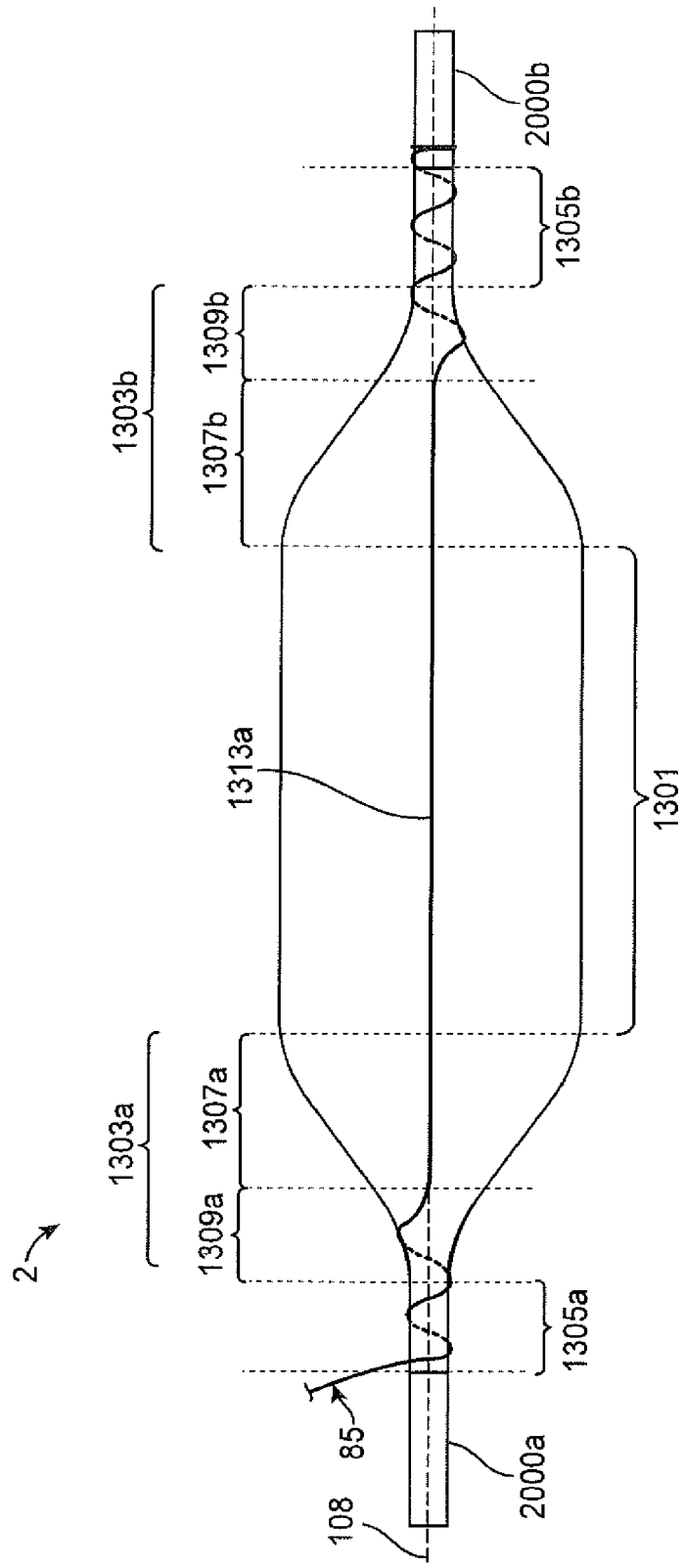
FIG. 2 shows the application of a first longitudinal fiber strand to an inflatable device.

Referring to FIGS. 2-7, in some embodiments, the strands 1313, 1315 can all be applied to the balloon as part of a single continuous fiber 85 (which can be a single monofilament or a fiber tow including a plurality of monofilaments). Referring to FIG. 2, the fiber 85 can be applied to a mandrel configured with the shape of the inflatable element 2 (i.e. with a central portion 1301, conical portions 1303a,b, and end portions 1305,a,b). The mandrel can further include sacrificial shafts 2000a,b extending from the ends of the inflatable element 2. The fiber 85 can be wrapped radially around the end portion 1305b, radially around through at least a portion of the conical portion 1303b, laid across the central portion 1301 substantially parallel to the longitudinal axis 108, and then extend down the cone portion 1303a where it can transition to wrapping radially around the cone portion 1303a and end portion 1305a. The first traverse across the length of the inflatable element 2 can form a first fiber strand 1313a.

Figure 3:
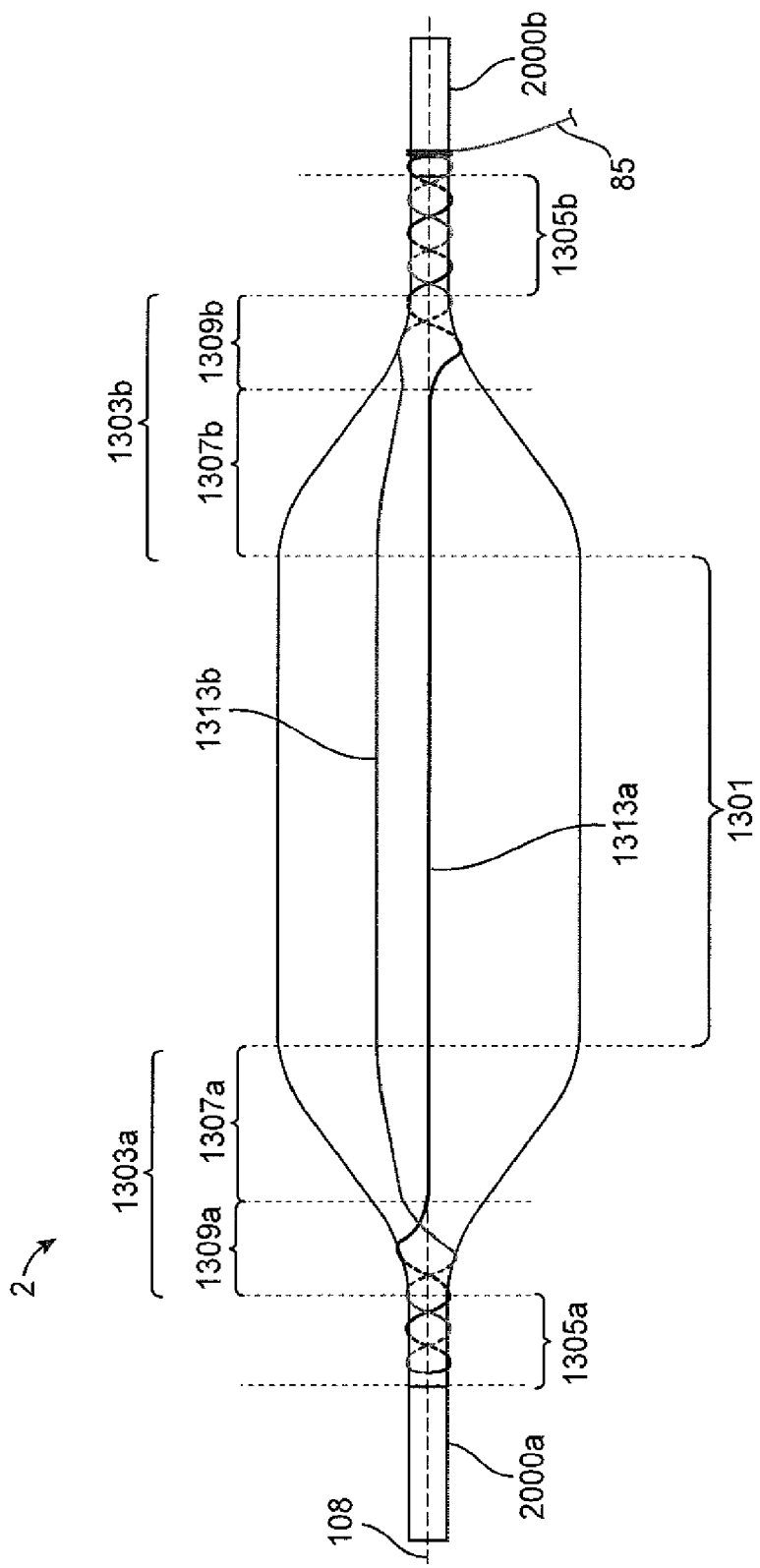
FIG. 3 shows the application of a second longitudinal fiber strand to an inflatable device.

Referring to FIG. 3, in order to form another fiber strand 1313b, the fiber 85 can be directed back towards the inflatable element 2 and wrapped in the opposite direction (i.e., from the end portion 1305a to the end portion 1305b). As shown in FIG. 3, the radial wrap (e.g., spiral or helix) of the fiber strand 1313b will extend opposite to that of the radial wrap of the fiber strand 1313a such that the strands 1313a,b meet or overlap a center point of each turn of the wrap. The fiber strands 1313a,b will further cross within the conical portion 1303a,b before straightening out to extend substantially parallel to one another within the central portion 1301.

Figure 4:
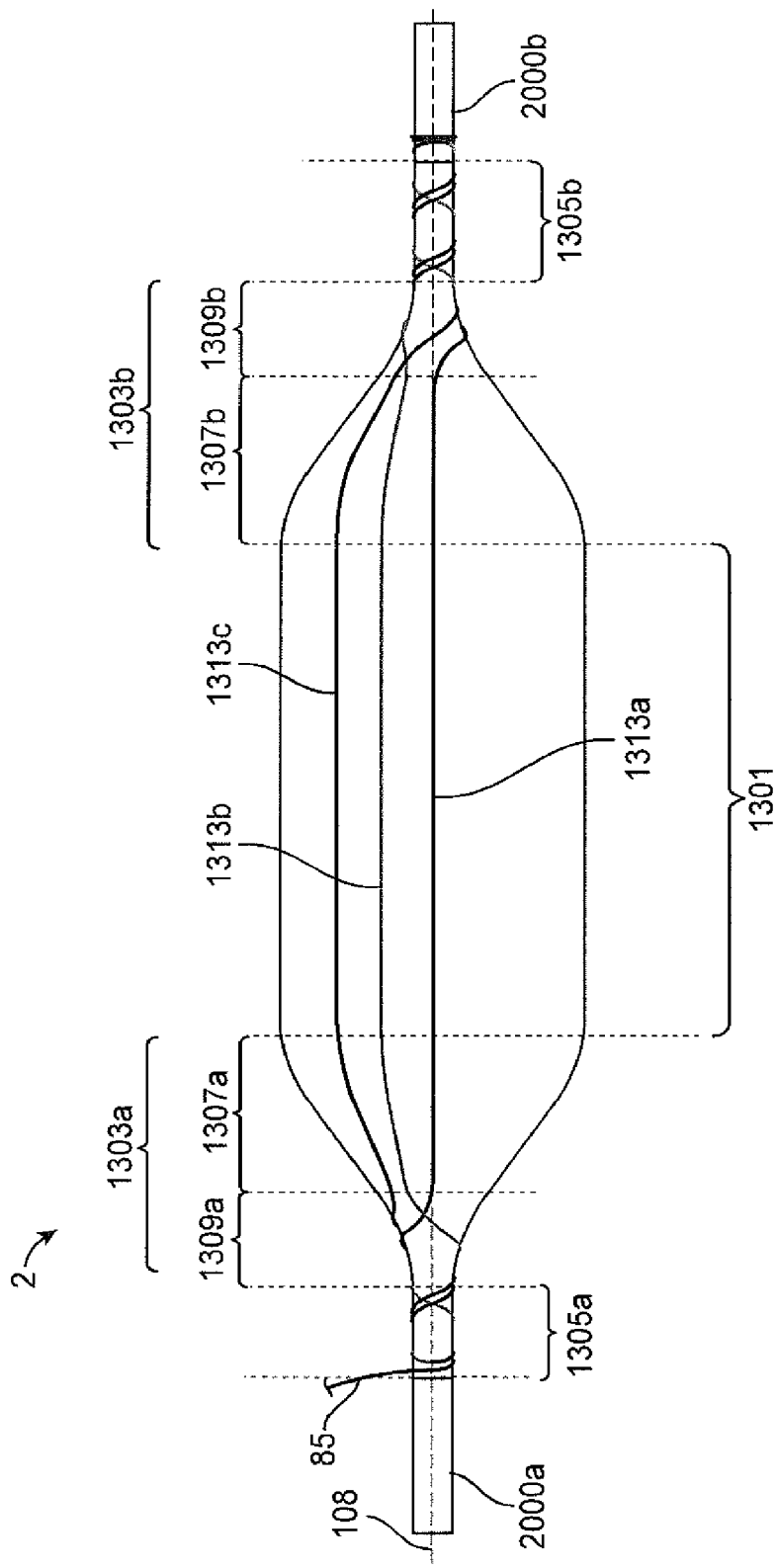
FIG. 4 shows the application of a third longitudinal fiber strand to an inflatable device.

Referring to FIG. 4, a third fiber strand 1313c can be applied by directing the fiber 85 back towards the inflatable element 2 and laying it down similar to fiber strand 1313a. As shown in FIG. 4, the fiber strand 1313c will run substantially parallel with the fiber strand 1313a along both the central portion 1301 and the end portions 1305a,b. Further, as shown in FIG. 4, the fiber strands 1313 can be laid down consecutively such that fiber strand 1313c is laid directly next to fiber strand 1313b, which his laid directly next to fiber strand 1313a.

Figure 5A:
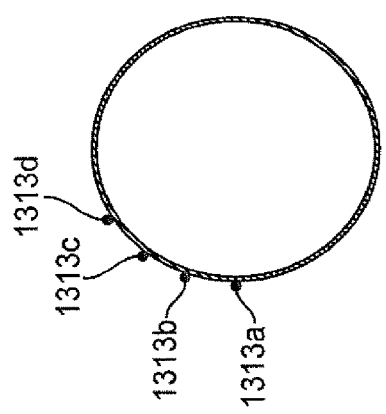
FIG. 5a is a cross-section of the inflatable device of FIG. 5.
Figure 5:
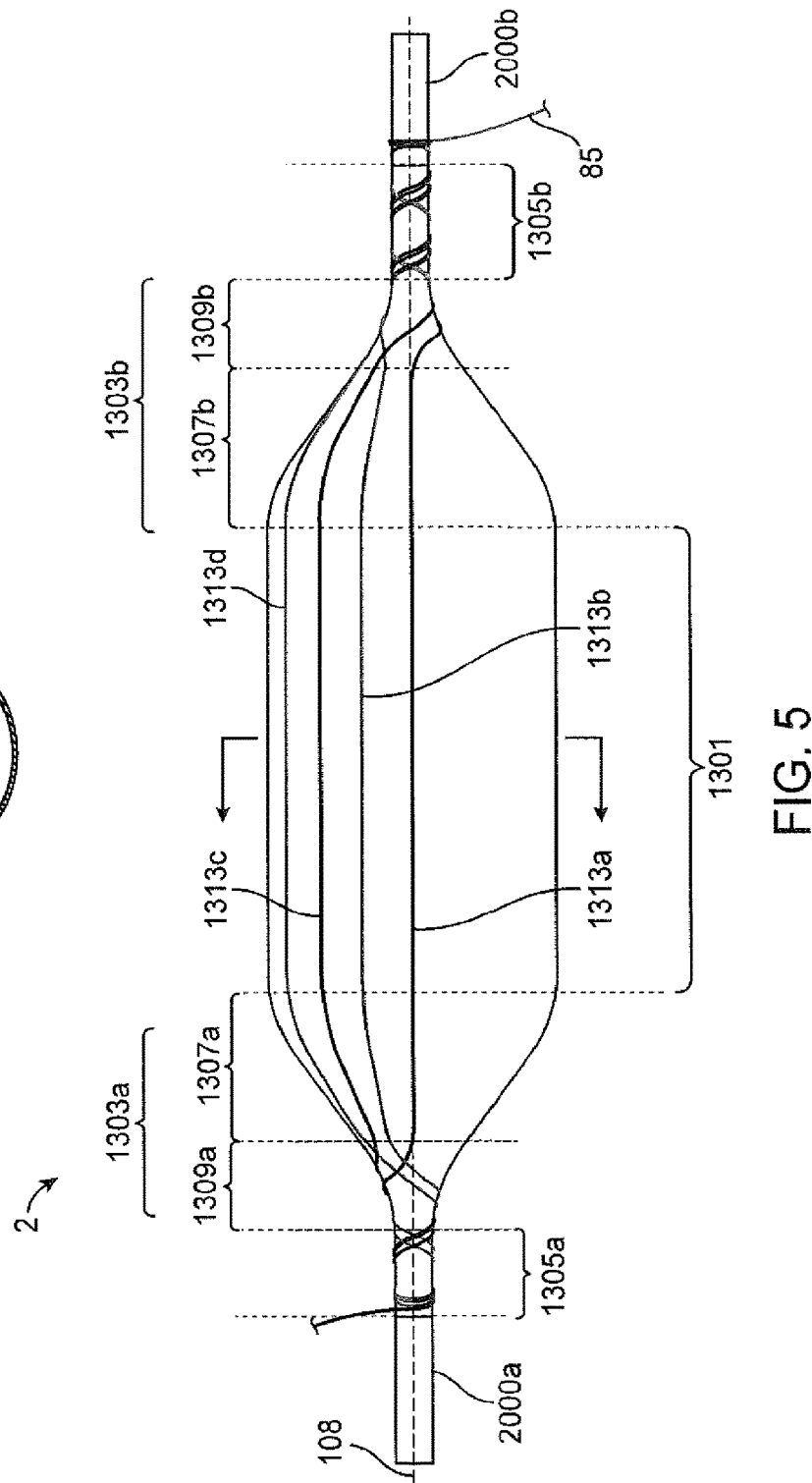
FIG. 5 shows the application of a fourth longitudinal fiber strand to an inflatable device.

Referring to FIG. 5, a fourth fiber strand 1313d can be applied by directing the fiber 85 back towards the inflatable element 2 and laying it down similar to fiber strand 1313b. FIG. 5a shows a cross-section of the resulting fiber lay-out.

Figure 6A:
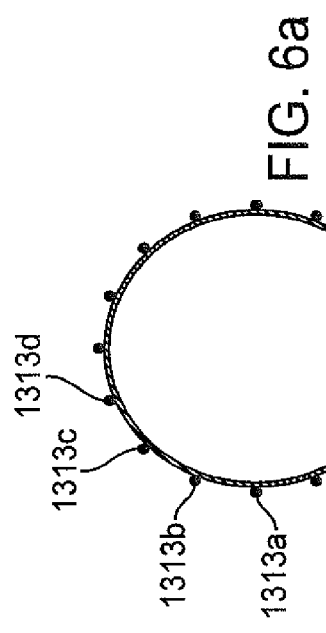
FIG. 6a is a cross-section of the inflatable device of FIG. 6.
Figure 6:
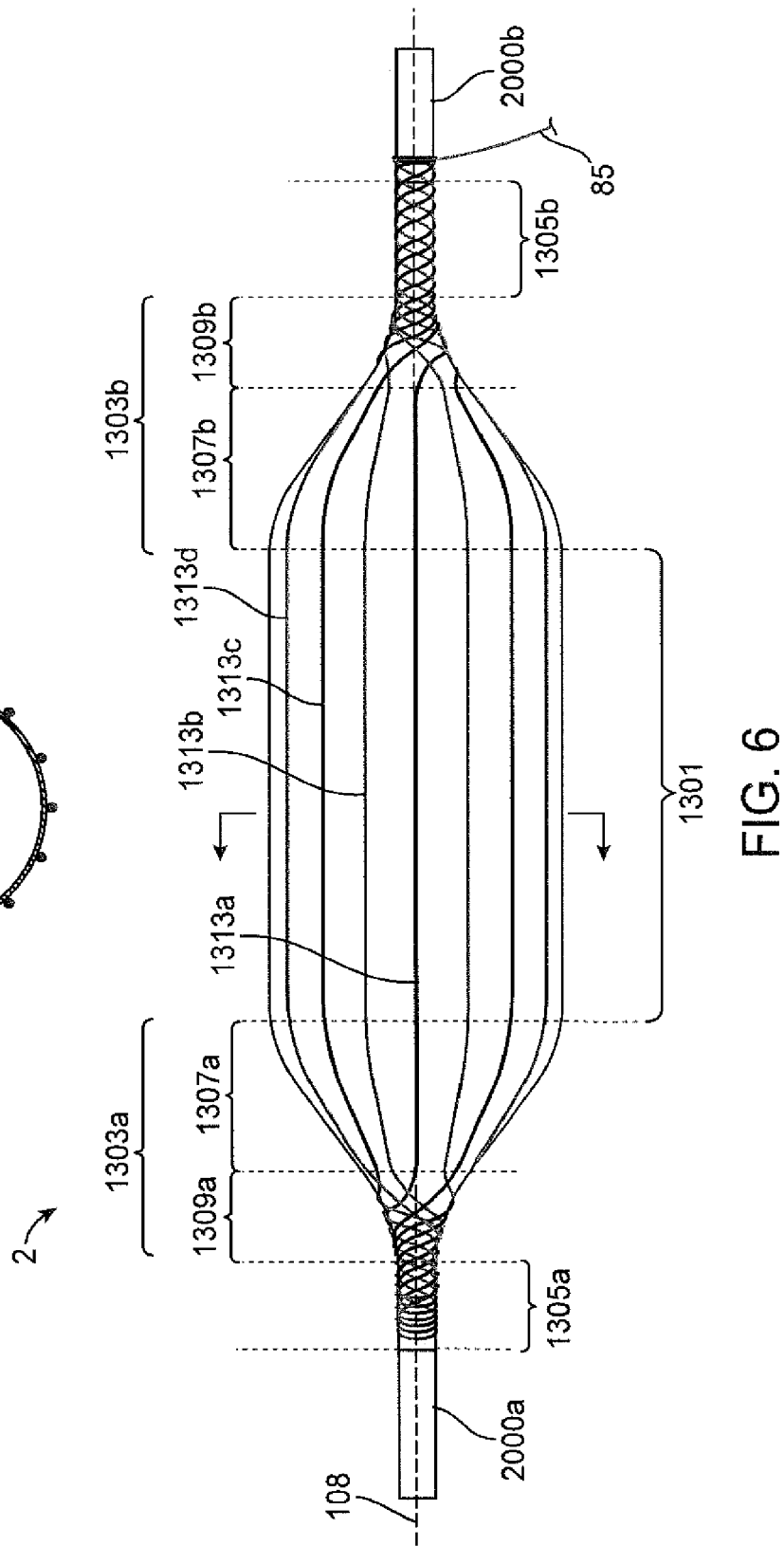
FIG. 6 shows longitudinal fibers extending all the way around the circumference of an inflatable device.

Referring to FIGS. 6 and 6a, the fiber 85 can continue to be wound back and forth from one end of the inflatable device to the other end until the fiber strands 1313 have been laid all the way around the circumference of the central portion 1301. The fiber strands 1313 can be laid down such that, when the entire circumference is covered, the fiber strands 1313 are substantially evenly spaced from one another throughout the length of the balloon. Thus, as the diameter narrows, the spacing between fiber strands will be reduced in amount, but still stay substantially even from fiber strand to fiber strand.

It should be understood that while only 12 strands 1313 have been shown around the circumference of the central portion 1301 for clarity purposes, the pitch of the strands 1313 can be much higher. For example, the pitch of the strands 1313 can be between 8 and 100 pitch, more narrowly, 30 and 50 pitch, such as approximately 40 pitch. Further, although the fiber strands were described as being laid down consecutively, they need not be. For example, the strands 1313 might be laid down in separate groups.

Figure 7A:
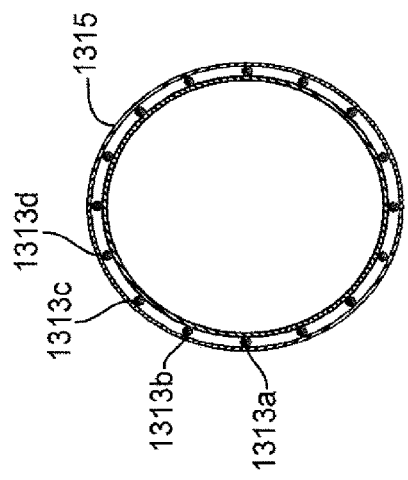
FIG. 7a is a cross-section of the inflatable device of FIG. 7.
Figure 7:
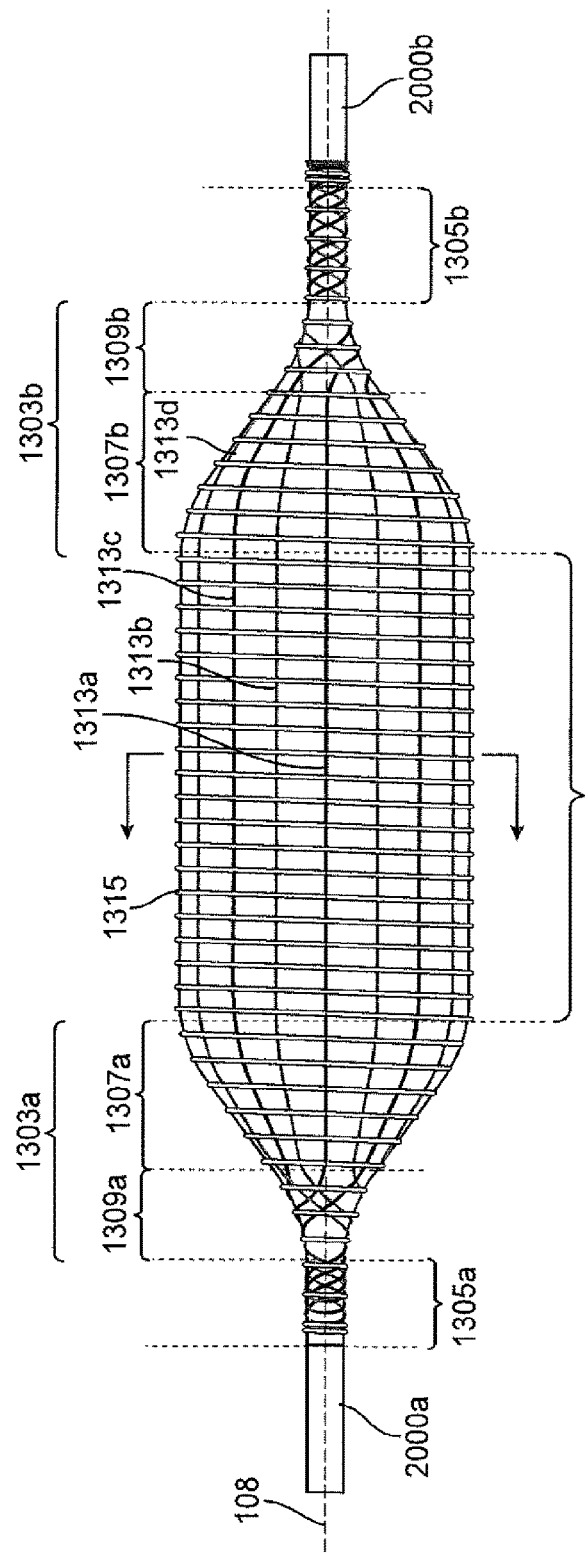
FIG. 7 shows a hoop strand wound around an inflatable device having longitudinal fiber strands thereon.

In some embodiments, the hoop strand 1315 can be applied using the same continuous fiber 85. In one embodiment (shown in FIGS. 7 and 7a), the hoop strand 1315 can be applied over all of the longitudinal strands 1313. Thus, once the longitudinal strands 1313 have been wound, the fiber 85 can be directed back towards the inflatable device 2 and wound radially around the end portions 1305a, b, the conical portions 1303a,b, and the central portion 1301 to form an overlaying hoop strand 1315.

Figure 10A:
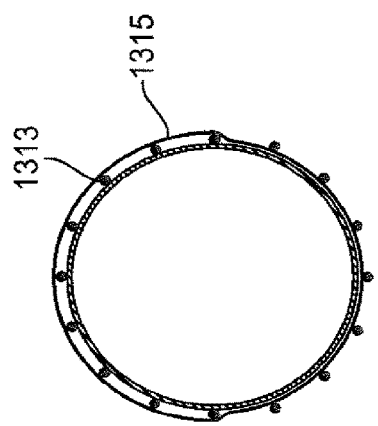
FIG. 10a is a cross-section of FIG. 10.
Figure 10:
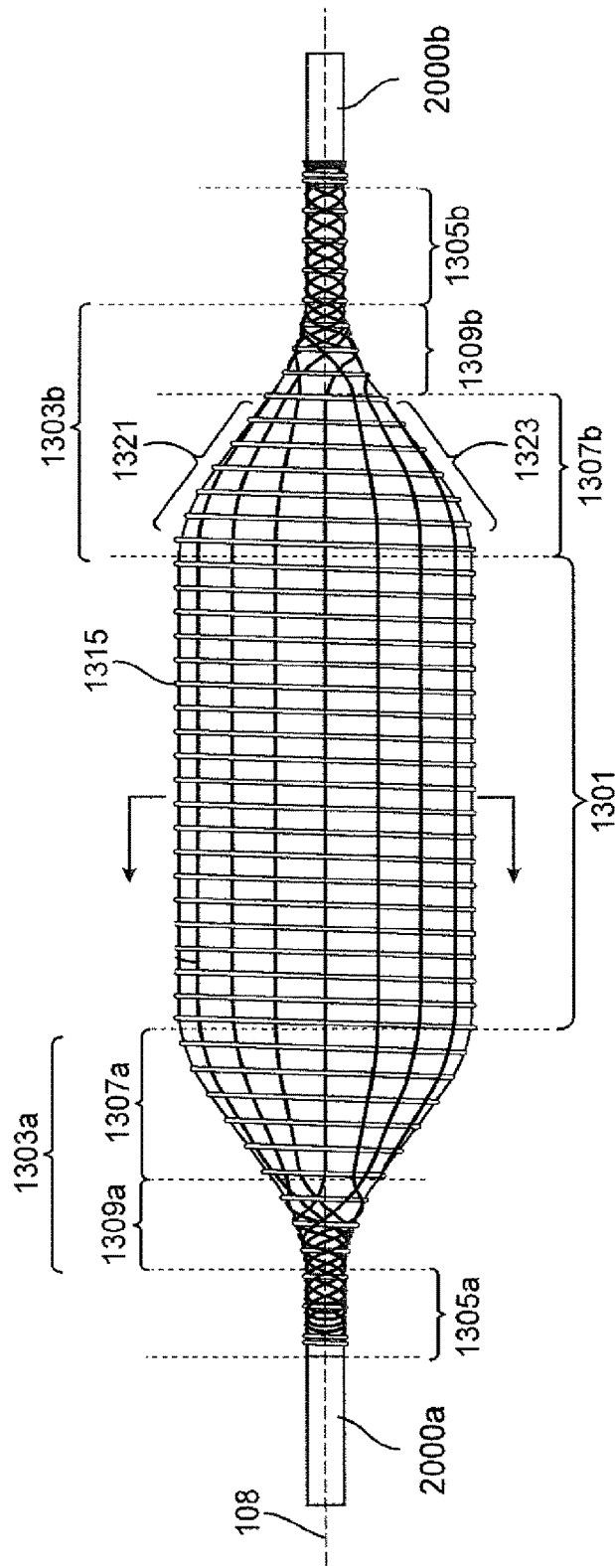
FIG. 10 shows application of longitudinal fiber strands over the hoop strand of FIG. 9.

Referring to FIGS. 8-10, in one embodiment, rather than applying the hoop strand 1315 over all of the longitudinal strands 1313, a set of the longitudinal strands 1313 can be placed down, followed by the hoop strand 1315, followed by a second set of the longitudinal strands 1313. For example, as shown in FIGS. 8 and 8a, the fiber 85 can be laid down along half of the inflatable device 2 to form a first set 1321 of strands 1313. As shown in FIGS. 9 and 9a, the fiber 85 can then be radially wound around at least the central portion 1301 to form the hoop strand 1315 over the first set 1321. Finally, as shown in FIGS. 10 and 10a, the fiber 85 can be laid down along the second half of the inflatable device 2 to form a second set 1323 of strands 1313 over the hoop strand 1315. As a result, the first set of fibers 1321 (extending along one half of the balloon) are underneath the hoop strand 1315 while a second set of strands 1323 are over the hoop strand 1315.

Figure 11:
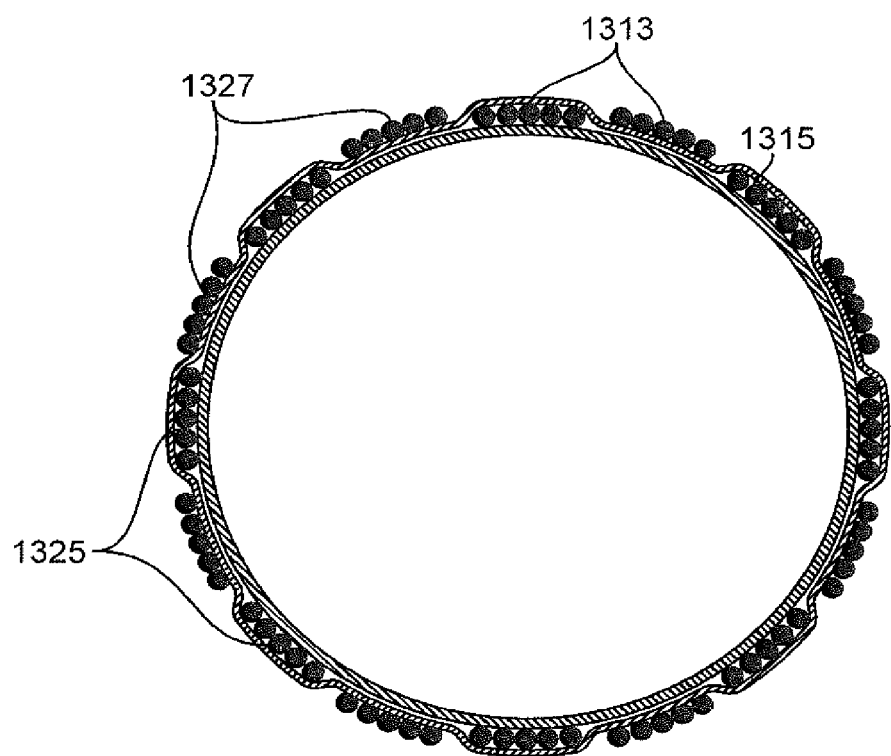
FIG. 11 is a cross-section of an inflatable device having groups of longitudinal strands under a hoop fiber strand and other groups of longitudinal strands over the hoop strand.

Alternate configurations are possible. For example, as shown in FIG. 11, a first set 1325 of the longitudinal strands 1313 could be laid down in a more spread out configuration (i.e. at half the pitch than is desired for the final device layup), then the hoop strand 1315 can be laid down, and then a second set 1327 of the longitudinal strands 1313 can be laid down over the hoop strand 1315 and in between the previously laid down longitudinal strands 1313. In this example, the first and second sets 1325, 1327 of longitudinal fiber strands 1313 could be laid down singularly or in groups (such as 1-10 longitudinal strands 1313 per group). In yet another example, the application of the hoop strand(s) can be separated by one or more application of longitudinal strands. For example, a hoop strand 1315 could be wound from one end to center over a set of longitudinal strands 1313, more longitudinal strands 1313 could be applied over the hoop strand 1315, and then another hoop strand 1315 could laid down from the other end to center.

Figure 12:
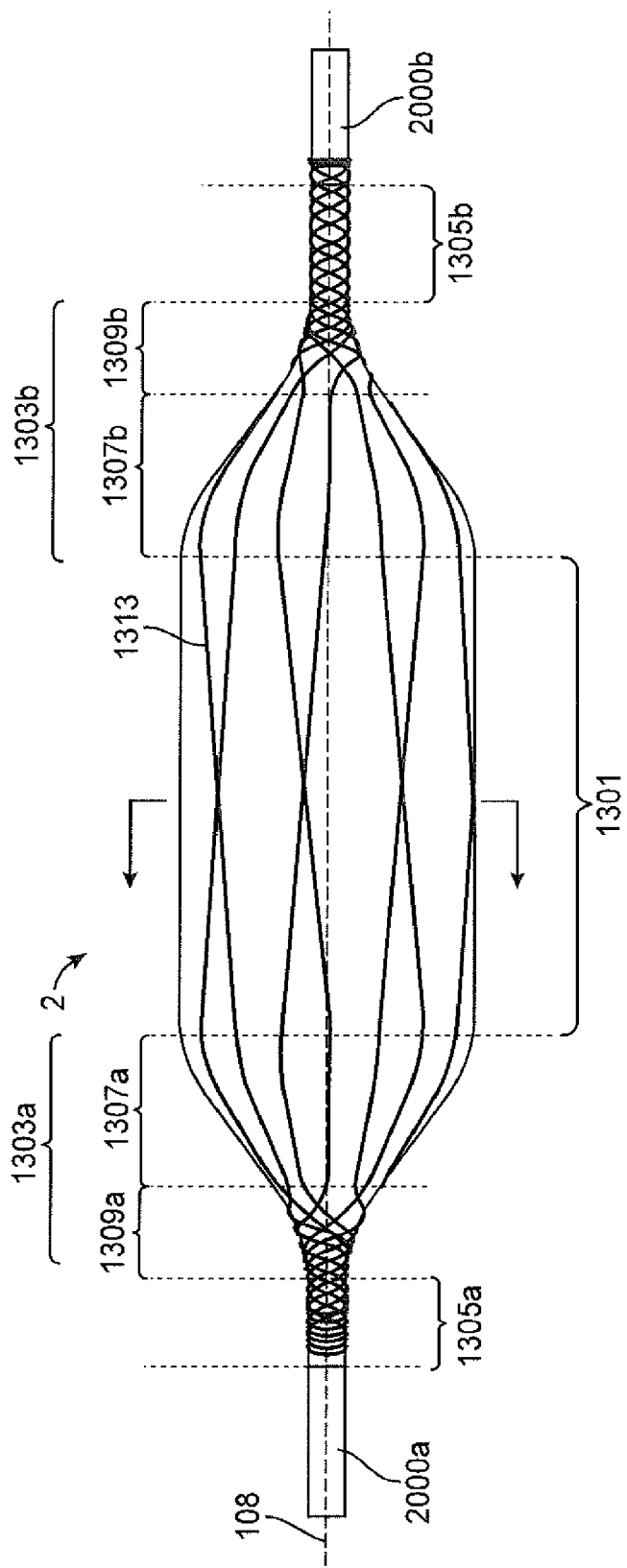
FIG. 12 shows longitudinal strands extending over an inflatable device at an angle to the longitudinal axis within a central portion of the inflatable device.
Figure 13:
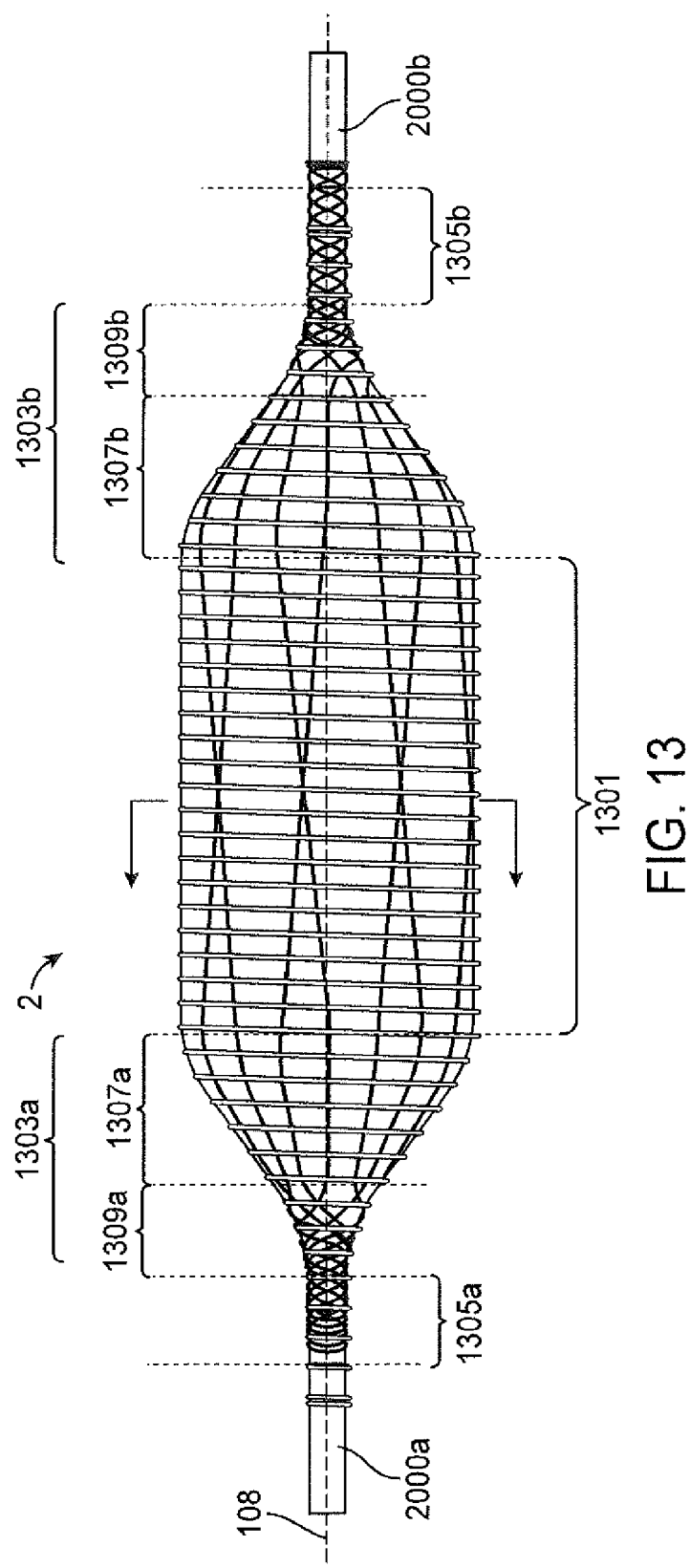
FIG. 13 shows a hoop strand wound over the inflatable device of FIG. 12.

Referring to FIG. 12-13, in some embodiments, the longitudinal fiber strands 1313 can extend at a slight angle relative to the longitudinal axis 108 within the central portion 1301. For example, the fiber strands 1313 can extend at an angle of +/−0 to 20 degrees relative to the longitudinal axis, such as +/−5-15 degrees, such as, for instance, +/−12 degrees. Further, every other fiber strand 1313 (or alternating groups of fiber strands) can extend in opposite positive/negative directions relative to the longitudinal axis 108, thereby keeping the inflatable device 2 from twisting.

Figure 14:
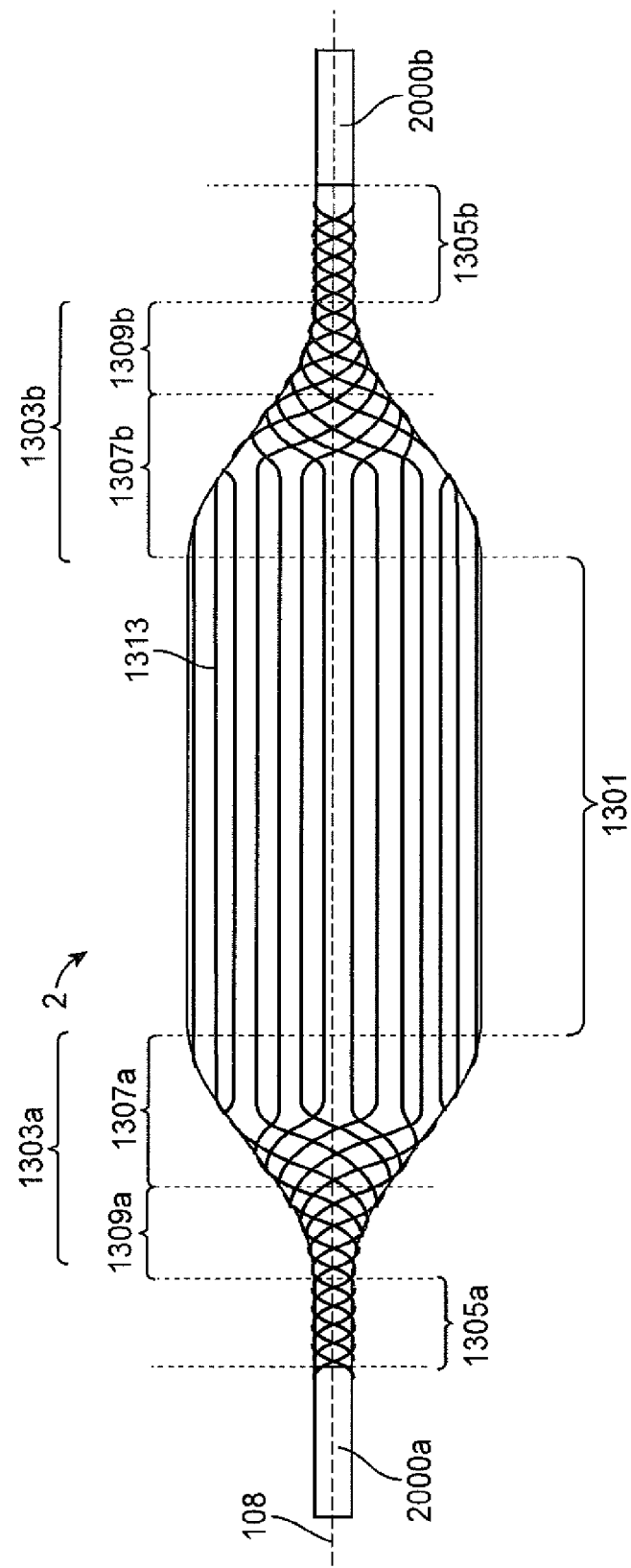
FIG. 14 shows an exemplary fiber wind on an inflatable device where the radial wrap of the longitudinal strands extends at least half way up the conical portions of the inflatable device.
Figure 15:
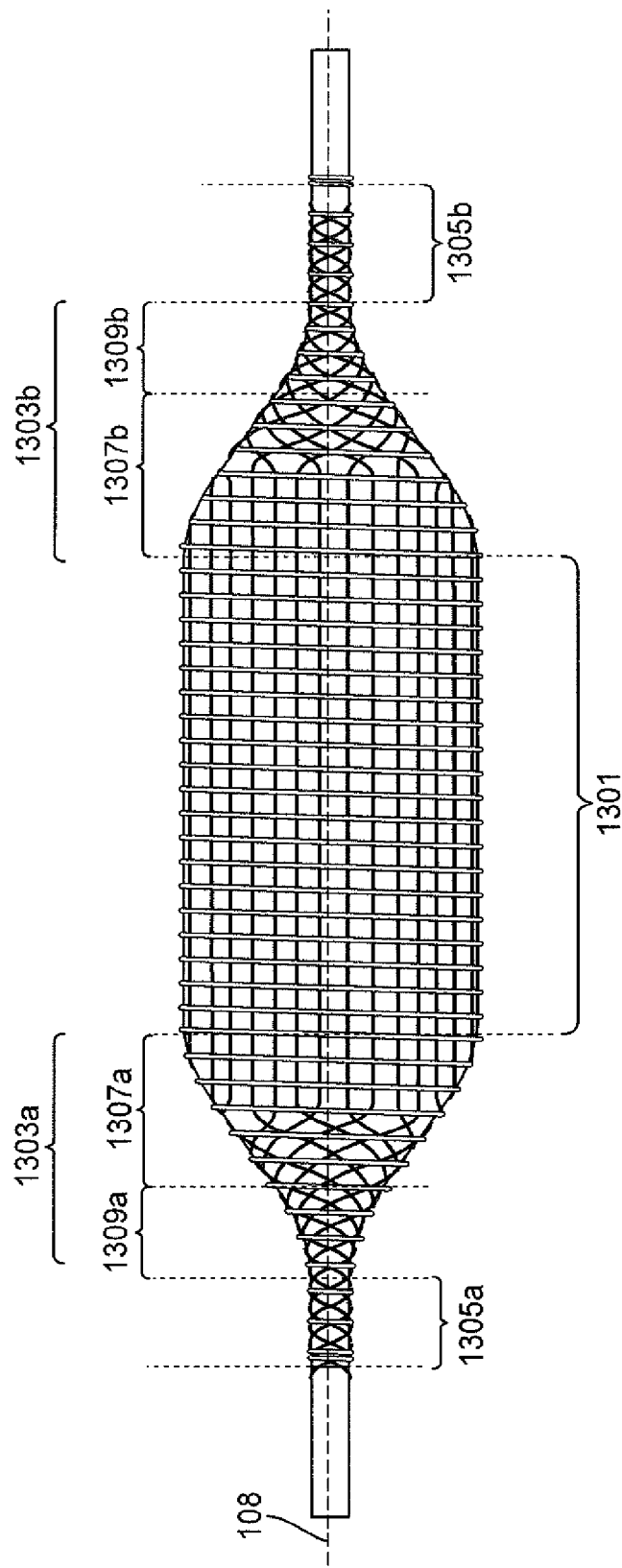
FIG. 15 shows a hoop strand wound over the inflatable device of FIG. 14.

Referring to FIG. 14-15, in some embodiments, the longitudinal fibers 1313 can extend radially around most or all of the concave subsections 1309a,b. Having the longitudinal fibers 1313 extending radially around the concave subsections 1309a,b can advantageously both help prevent the fiber strands from lifting up during or after application of the strands (as fiber strands extending substantially parallel to the longitudinal axis tend to want to lift up out of the concave section) and help prevent the fiber strands from falling down the steep angle during or after (as fiber strands extending substantially perpendicular to the longitudinal axis tend to want to fall down the slope). In other embodiments, the radial wind of the longitudinal strands 1313 can extend less than 1%, about 10%, 20%, 30%, 40%, 50%, 60%, 70%, 80%, 90%, or 100% of the length of the conical portions 1303a,b.

In some embodiments, rather than having each longitudinal strand extend the entire length of the inflatable device, the longitudinal strands can reverse or turn around in the conical portions. For example, some of the longitudinal strands can reverse at the point where the rest of the longitudinal fibers go from being substantially parallel to the longitudinal axis to winding radially around. Advantageously, by having such strands that reverse within the cone rather than extending all the way to the end of the balloon, there can be less build-up of fiber in the ends of the cone.

In some embodiments, the longitudinal fiber strands 1313 can extend substantially parallel to the longitudinal axis 108 within the end portions 1305a,b. Thus, each strand can extend substantially parallel to the longitudinal axis 108 within the central portion 1301, radially around at least part of the conical portions 1303a,b, and substantially parallel to the longitudinal axis 108 within the end portions 1305a,b.

The sacrificial shafts 2000a,b can be removed after all of the fiber has been applied. In some embodiments, a portion of the inflatable device and/or shaft over which fiber has been applied can be cut off. Doing so can advantageously remove unnecessary thickness at the turnarounds. Thus, during application, the turnaround point for some or all of the strands 1313 (i.e. the connection from one strand to the next strand) can be laid down either over the sacrificial shafts 2000a,b or over the inflatable device 2 itself. In FIGS. 2-10 and 12-16, the fiber is shown as extending over the sacrificial shaft 2000b and ending before the sacrificial shaft 2000a.

The fiber strands described herein can be part of a fiber matrix, such as fibers extending within a resin, adhesive, or thermally weldable material (such as a TPU). The resin, adhesive, or thermally weldable material may be applied to the fibers before, during, or after the fibers are placed on the inflatable device 2.

Figure 17:
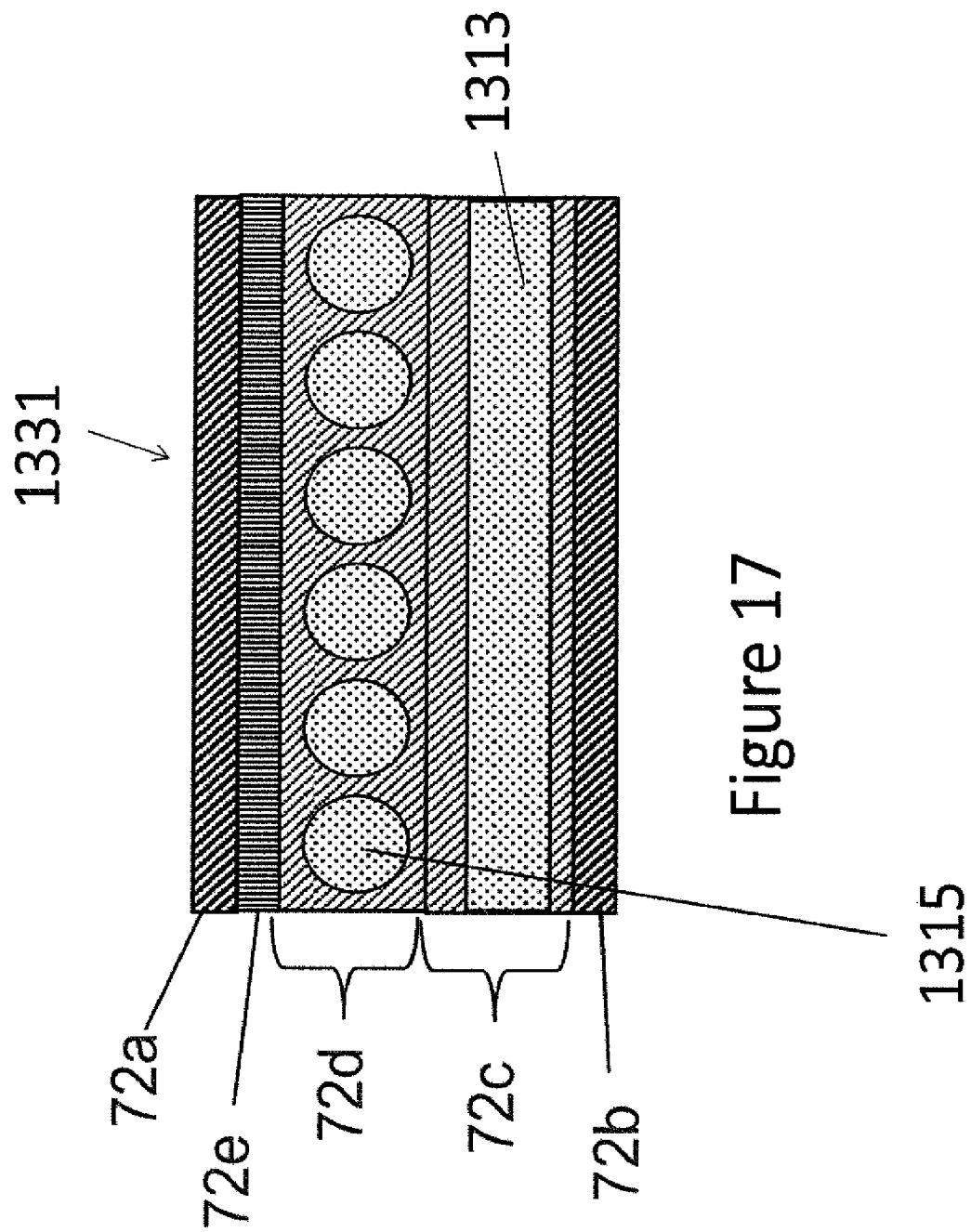
FIG. 17 shows exemplary layers or sections of the wall of an inflatable device.

The inflatable device 2 described herein can include additional radial sections aside from those described herein. For example, referring to FIG. 17, the inflatable device can include a wall 1331 having an outer layer 72a, such as a polymer film. The wall 1331 can further include an inner layer 72b, which can be a leak proof bladder made from a polymer film. The first middle layer 72c can be a fiber matrix, for example with the fibers 1313 as described above. The second middle layer 72d can be a fiber matrix, for example with the strands 1315 oriented both radially and parallel as described above. Additionally, as described above, the matrix layers 72c, 72d can be merged together into a single layer by having the hoop strands 1315 extend over some of the longitudinal strands 1313 and under other longitudinal strands 1313. Alternatively, the matrix layers 72c, 72d can be switched in orientation relative to one another. The third middle layer 72e can be a resin or adhesive or thermally weldable material. The outer layer 72a may serve to isolate and protect the strands 1313, 1315.

Figure 18A:
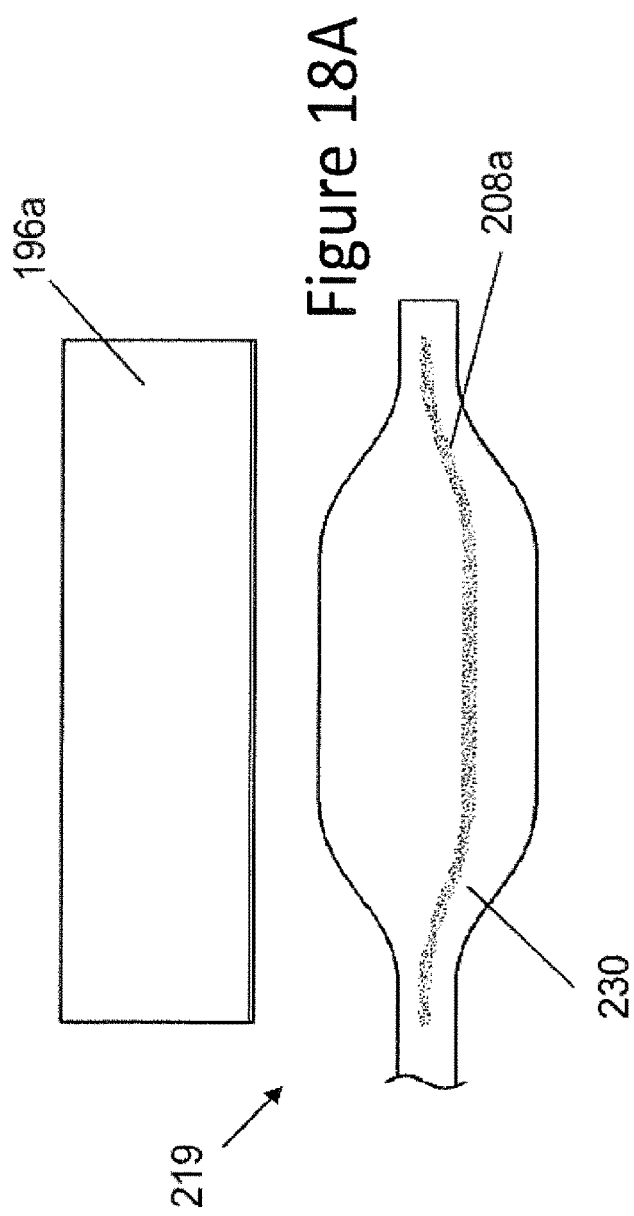
FIGS. 18A-18G shows an exemplary method of making an inner layer or bladder for an inflatable device.

To manufacture the entire balloon wall 1331, a bladder can first be created. For example, referring to FIGS. 18A-18G, the bladder can be made over a mandrel 230 having the shape of the inflatable device 2 (i.e., a central portion, conical portions, and end portions). FIG. 18A illustrates that the outer surface of the mandrel 230 can have some glue or first adhesive 208a. The first adhesive 208a can be located around the perimeter of the first panel's 196a contact area with the mandrel. The first adhesive 208a can be water soluble. The first adhesive 208a can be a sugar syrup. A panel 196a may be positioned over the mandrel. The panel 196a may be a single layer or multiple layers. For instance, the panel could be a layer of film and meltable adhesive. The panel 196a can be positioned with film on the side that touches the mandrel and adhesive on the radially outer side. The panel 196a may be perforated. The panel may not be capable of sustaining pressure between the top and bottom of the panel.

Figure 18B:
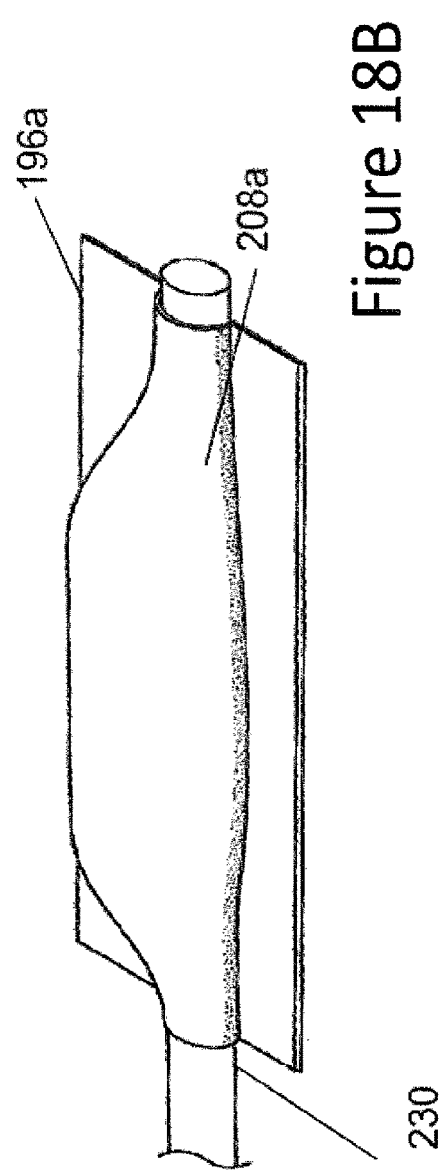

FIG. 18B illustrates that a positive pressure can be applied to the top of a pressure chamber and/or a negative pressure or differential pressure or suction or vacuum applied to the bottom of a pressure chamber. As a result, the panel 196a can get sucked and/or pressed down and/or formed onto the mandrel 230. Forming of the panel 196a may cause portions of panel 196a to yield or stretch or deform or become thinner or combinations thereof. For instance, more than about 25% of the panel 196a covering central section 38 may have been significantly yielded and/or stretched during the forming operation. The first panel can be smoothly fitted to the mandrel 230 and adhered to the mandrel at the first adhesive 208A. Heat may be applied to panel 196a before forming onto mandrel 230. Forming of one panel 196a may be done more than once on different sized mandrels before the panel 196a reaches the form shown in FIG. 18B. Forming of panel 196a may also be accomplished with a mechanical die. The mechanical die may be heated and conform closely to the shape of the mandrel 230. The mechanical die may have a shape similar to the mandrel. The mandrel 230 and panel 196a can be mounted into a trimming jig. Any excess portion of the first panel 196a extending from the mandrel 230 can be trimmed with a blade, with a laser, with a water jet cutter, with a die cut tool or combinations thereof. The trimming jig can cover the mandrel 230 and the first panel 196a attached to the mandrel. Several panels 196a and/or layers 72 can be formed over the mandrel 230 and cut. The panels 196a and/or layers 72 may be trimmed at the same time or one at time.

Figure 18C:
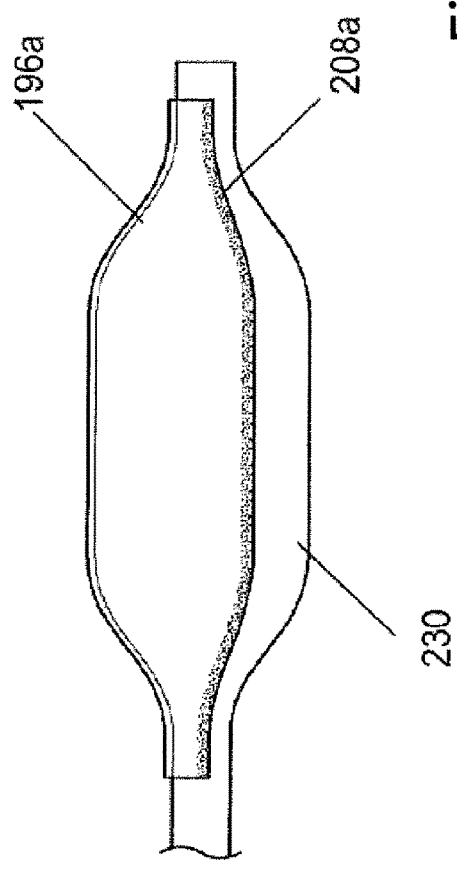

FIG. 18C illustrates that the mandrel can have the excess area of the first panel 196a removed in preparation for attachment of the second panel 196b.

Figure 18D:
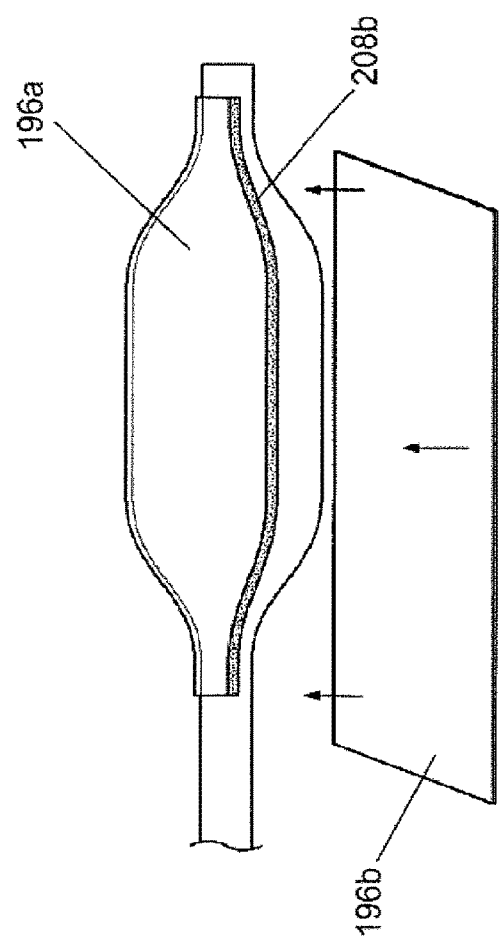

FIG. 18D illustrates that a second adhesive 208b can be applied to the first panel 196a around the perimeter of the second panel's 196b contact area with the first panel 196a. The second adhesive 208b can be an epoxy, urethane, a thermoplastic, a cyanoacrylate, a UV curing adhesive, or combinations thereof. The mandrel 230 can be seated in a mandrel seat with the first panel 196a in the mandrel seat. The second panel 196b can be placed on the mandrel 230 as shown.

Figure 18E:
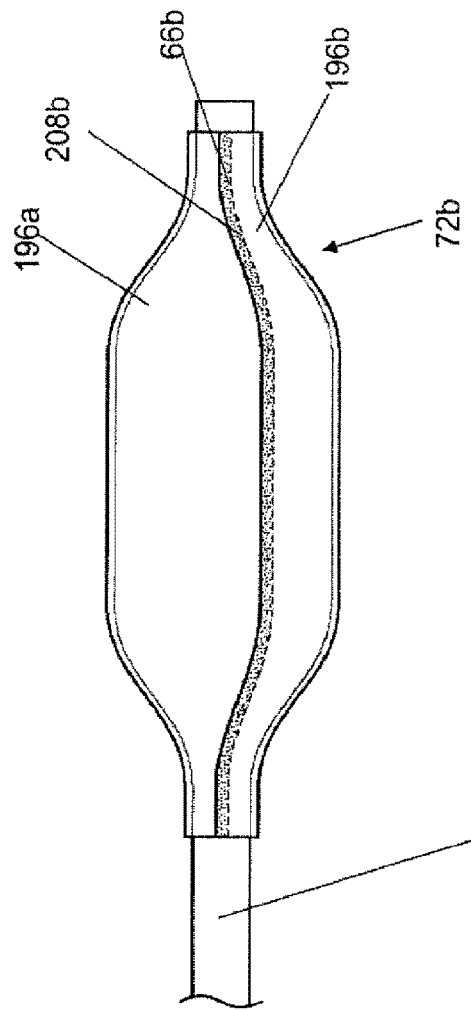
Figure 18G:
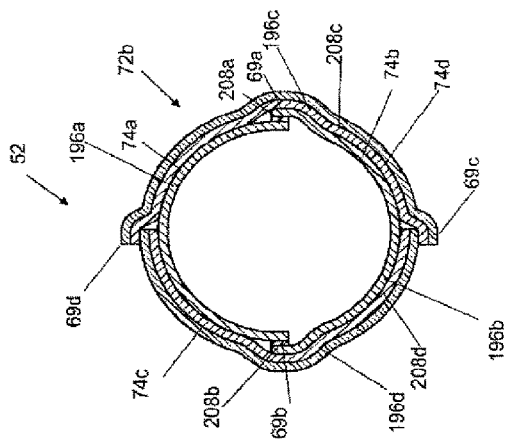

FIG. 18E illustrates that positive and/or negative pressures can be applied to the pressure chamber as described infra. The second panel 196b can be smoothly fitted or pressure formed to or against the mandrel 230 and adhered to the first panel 196a at the second adhesive 208b. Adhesion can be accomplished by the application of heat. The first and second panels (196a and 196b) can form the inner layer 72b or bladder 52 of the balloon wall. The inner layer may be leak tight. The inner layer may be capable of sustaining pressure. Multiple layers can be made by repeating the method described infra. The pressure chamber can be heated, for example, to decrease the viscosity of and decrease the modulus of the panels.

Figure 18F:
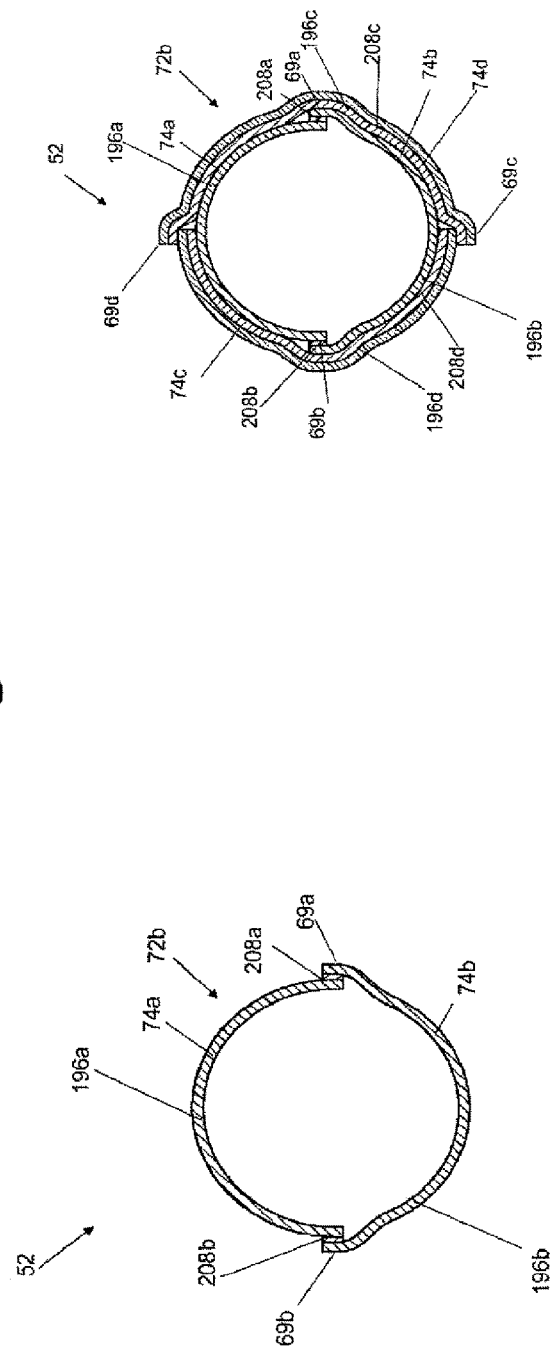

FIG. 18F shows a cross section of 32E with the mandrel 230 omitted. The process in FIGS. 18A through 18E may be repeated on the part shown in FIGS. 18E and 18F to produce the bladder 52 cross section shown in FIG. 18G. Panels 196c and 196d may be formed. Each panel may have an adhesive 208c and 208d facing radially inward. Balloon third and fourth internal seams 69c and 69d may be oriented about midway between balloons first and second internal seams 69a and 69b. The bladder 52 may be leak tight. Alternatively, the inner layer can be a blow-molded balloon, which is well-known in the art. The balloon can be filled with media (gas, liquid, or solid) during the winding process.

Figure 16:
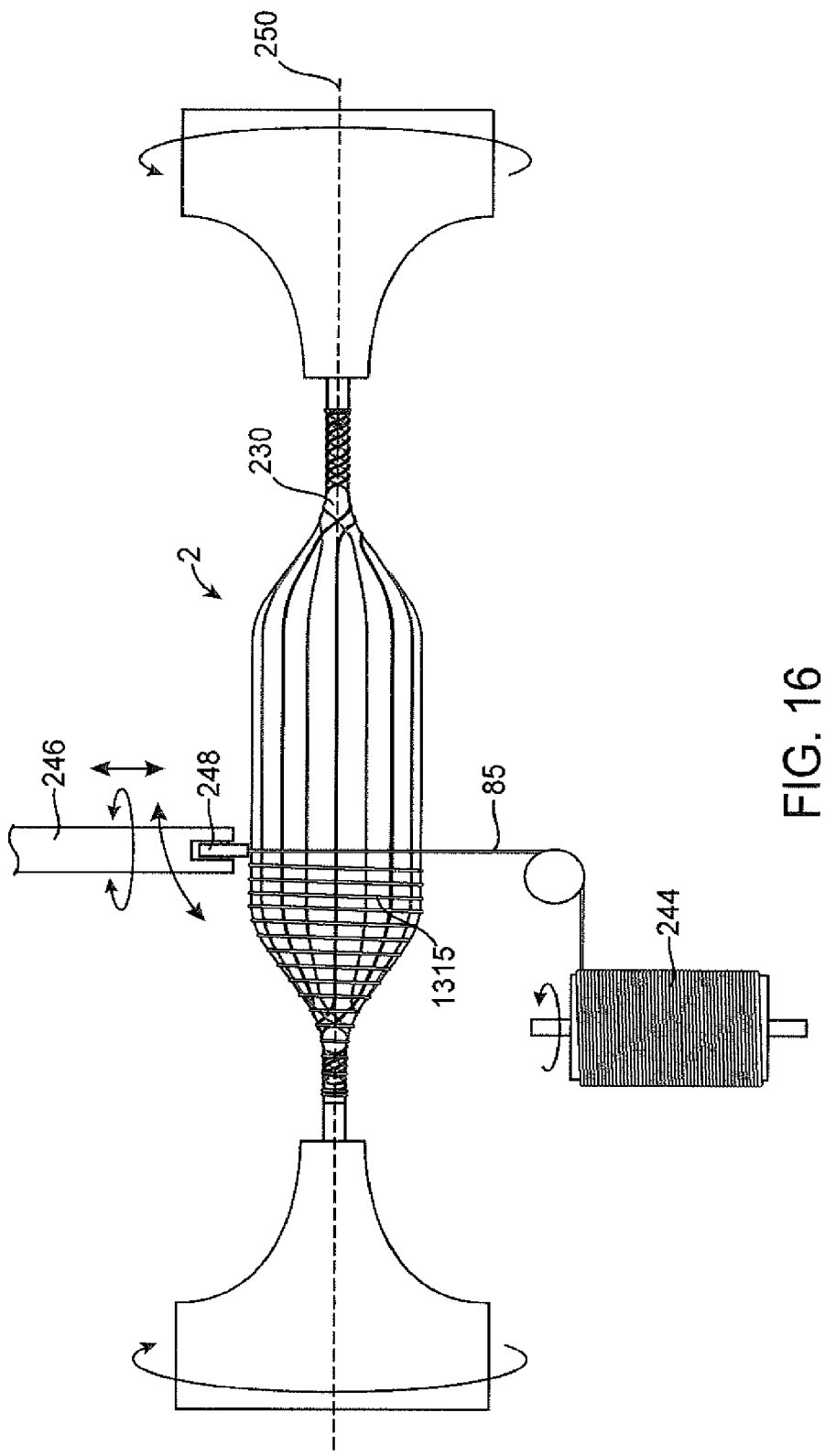
FIG. 16 shows application of fiber strands to an inflatable device in a continuous process with a tool wheel.

Referring to FIG. 16, the fiber 85 can then be applied over the bladder or mandrel. The fiber 85 can be applied, for example, using an automated head configured to run the fiber across the surface of the bladder or mandrel. FIG. 16 illustrates that fiber 85 can be wound over a mandrel 230 (which can include bladder or other layers thereon) using a tool wheel 248. The fiber 85 may be continuous or discontinuous. The mandrel can be rotated about the mandrel longitudinal axis 250 or balloon longitudinal axis. The mandrel can be rotated, for example, in a single direction throughout the entire fiber-laying process so as to obtain the fiber pattern depicted in FIG. 1.

The spool 244 can be passively (e.g., freely) or actively rotated, deploying fiber 85. Before or during winding, the fiber 85 may be infused or coated with an adhesive, a solvent, or both. A tool arm 246 can be attached to a rotating tool wheel 248. The tool arm 246 can rotate and translate to position the tool wheel 248 normal to and in contact with the inflatable device 2. The tool wheel 248 can apply pressure normal to the surface of the inflatable device 2 so as to help attach the fiber 85 to the surface upon which it is being applied and/or spread monofilaments of the fiber tow across the device. The tool wheel 248 may help to adhere the fiber 85 to the inflatable device 2, for example by applying pressure and following closely the surface of the inflatable device 2 or mandrel 230. The tool wheel 248 can be heated to soften or melt the material on the surface of the balloon 20. Another heat source or a solvent may be used to tack the fiber in place, to melt or solvate a material on the balloon, to melt or solvate a material on the fiber or combinations thereof. A separate resistive heater, a laser, a UV light source, an infrared light source, a source of hot air, or an RF welder may be used with or without the tool wheel 248 to attach the fiber. A solvent such as methyl ethyl ketone or tetrahydrofuran or alcohol or combinations thereof may promote adhesion of the fiber 85 and may be used with our without the tool wheel 248. The tool wheel 248 can be made of or coated with a non-stick material. The tool wheel 248 may not rotate. The tool wheel 248 may comprise a hard surface, for example carbide. In some embodiments, a nozzle having a hard surface can be used in place of the tool wheel 248.

In some embodiments, an adhesive or thermally weldable material, such as thermoplastic polyurethane (TPU), can be applied to the bladder to help stick the fiber thereto. Further, in some embodiments, the fiber can be dipped through a solvated adhesive or thermally weldable material, such as TPU, during the application. In some embodiments, the material can be applied by spraying. In cases where both solvated thermally weldable material and thermally weldable material on the bladder are used, the native thermally weldable material can advantageously meet the solvated thermally weldable material to help aid the adhesive properties. Adhesive or thermally weldable material can be applied during application of fiber or after the wind is concluded.

Further, in some embodiments, an outer layer can be applied over the fiber wind. The outer layer can be formed, for example, of a panel or panels of film wrapped around the fiber-covered device, similar to described and shown with respect to FIGS. 18A-18E.

In some embodiments, the inner or outer layers described herein can be formed by deposition. For example, a metal such as gold (or other materials listed herein) may be deposited to form a layer. The layers may be formed by vapor deposition, such as physical vapor deposition, chemical vapor deposition or combinations thereof. For example, materials such as parylene, polyimide, polynapthalene, Polyphenylene Vinylenes, fluoropolymer blends, Polyazomethine, poly-fluorohycrocarbons, poly-perfluorocarbons, polyolefins, or combinations thereof may be deposited. Vapor deposited layers can advantageously be pinhole free, thereby enhancing the leak-resistance of the inflatable device. Furthermore, vapor deposition allows for the layers to be easily mass-produced.

After all of the layers of the wall 1331 have been applied to the mandrel, the wall 1331 can be consolidated. For example, referring to FIGS. 19A-19B, the inflatable device 2 before final consolidation may be placed in a balloon mold 622 containing a balloon pocket 624. The balloon mold may be textured or porous such that substantial amounts of gas may be drawn from balloon pocket 624 through or along the wall of balloon mold 622 and out into the surrounding atmosphere. The balloon may have a tube placed in its inner volume that may extend out either end of the balloon 622 (not shown). The tube may be thin and very flexible. The tube may be a silicon rubber. A coating may be sprayed into mold 622 that bonds to the balloon during cure to form an outer layer 72a on the balloon 2.

FIG. 19B illustrates that the balloon mold may be closed around the inflatable element 2. Pressure may be applied thru balloon second fluid port such that the balloon expands to contact the inside of balloon pocket 624. Alternately, the tube extending out either end of the balloon (not shown) may be pressurized to force the balloon into contact with pocket 624.

Mold 622 may be placed in an oven and heated. Mold 622 may have built in heaters. The balloon mold may be placed under vacuum or placed in a vacuum chamber during heating. Heating the balloon under pressure may cause one or more layers or sections to melt and/or fuse and/or bond with adjoining layers or sections. The melting under pressure may remove voids or pockets in the balloon wall. The outer inner and outer layers (72b, 72a) may not melt. Heating the balloon under pressure may cause the wall 1331 of the inflatable device 2 before final consolidation to fuse or laminate into one continuous structure. The balloon outer wall 22b and/or outer layer 72a may be substantially smoothed by this process. The balloon outer wall 22b and/or outer layer 72a may be permeable or perforated such that gas or other material trapped in the balloon wall 22 during manufacture may escape when the balloon is heated under pressure.

The fibers described herein can be made from a variety of materials. Exemplary materials include Vectran®, PBO, Spectra®, Conex®, Dyneema®, Technora®, Dacron®, Compete, Polyester, Nylon, PEEK, PPS, Boron Fiber, Ceramic Fiber, Kevlar®, Inorganic Carbon or Carbon fiber, Inorganic silicon or high strength fiberglass, Organic polymer or aramid, Twaron®, Tungsten, Molybdenum, Stainless Steel, Nickel/cobalt alloys, Titanium alloys, and Nitinol alloys.

The inflatable devices 2 described herein can be used as medical invasive balloons, such as those used for transcutaneous heart valve implantation are disclosed. For example, those balloons used for transcatheter aortic-valve implantation. Inflatable device 2 may also be used for angioplasty in both coronary and peripheral applications.

In one exemplary embodiment, an inflatable medical device for use in BAV can have a diameter of approximately 20 mm, a burst pressure of around 10 atm, 40 tows per inch lengthwise in the central portion (about 126 tows in a one-inch diameter balloon), and 60 tows per inch in the hoop wind in the central portion. The tow can have 8 monofilaments and a break strength of about 1.4 lbs.

Advantageously, the inflatable device described herein is configured to help prevent helical or circumferential failures. That is, because the fibers extend substantially parallel to the longitudinal axis within the central portion of the device (which has the largest diameter), the device is most likely to fail along those parallel fibers in the central portion. Such failure substantially along the longitudinal axis can advantageously allow for ease of pull-out through a sheath or introducer. Should the central portion be helically wound, hoop fibers can be deposited at or near the shoulder such that the burst failure would be helical, but constrained to an increasingly narrow central zone.

Furthermore, the fiber strands of the inflatable device described herein can be laid down continuously with minimized tooling. The process can be automated and easily updated. The fiber application process can be performed quickly, particularly the application of the strands parallel to the longitudinal axis. Further, since the path of the machine is controlled by a computer running software, the automated process allows for ease of changeability between different size and shapes of inflatable devices. After a device is loaded, the application of all the fiber can be accomplished automatically, with no need for human intervention.

The inflatable device described herein can further be engineered to have fiber deposition that exhibits minimized internal wall shear. Wall shear may lead to "slumping" of fiber, wherein fibers, particularly hoop fibers, travel from larger radius sections to smaller radius sections when the balloon is inflated. Travel of hoop fibers may cause premature failure of the balloon and thus limit the balloon's maximum inflation pressure.

The fiber strands of the inflatable device described herein further allow for a decreased build-up of fibers at the ends of the balloon relative, for example, to a balloon wound with a helix pattern.

The fibers for the inflatable device described herein are further advantageously applied using slight tension throughout the entire application process, thereby helping to ensure that fiber doesn't lift or move during application.

Any elements described herein as singular can be pluralized (i.e., anything described as "one" can be more than one), and plural elements can be used individually. Characteristics disclosed of a single variation of an element, the device, the methods, or combinations thereof can be used or apply for other variations, for example, dimensions, burst pressures, shapes, materials, or combinations thereof. Any species element of a genus element can have the characteristics or elements of any other species element of that genus. The above-described configurations, elements or complete assemblies and methods and their elements for carrying out the invention, and variations of aspects of the invention can be combined and modified with each other in any combination.

The invention claimed is:

1. A medical apparatus, comprising:
an inflatable balloon including a central portion and first and second tapered portions connected to the central portion together forming an interior compartment for receiving an inflation fluid, the balloon including a longitudinal axis extending from a first end of the balloon to a second end of the balloon; and
a single continuous fiber extending substantially parallel to the longitudinal axis along the central portion, wherein the single continuous fiber has at least one turn around on at least one of the first and second tapered portions of the balloon.

2. The apparatus of claim 1, wherein the single continuous fiber has first and second turn arounds on at least one of the first and second tapered portions.

3. The medical apparatus of claim 1, wherein the single continuous fiber extends radially around at least a portion of the balloon, wherein the single continuous fiber extends radially around at least one of the first and second tapered portions, or wherein the single continuous fiber extends radially around the central portion of the balloon.

4. The apparatus of claim 3, wherein the single continuous fiber comprises a plurality of first fiber strands, wherein each strand of the plurality of first fiber strands extends at an angle of approximately 35-90 degrees relative to the longitudinal axis of the balloon as the plurality of first fiber strands extend radially around at least a portion of the first and second tapered portions, or wherein each strand of the plurality of first fiber strands transitions from extending radially around at least a portion of the tapered portions to extending substantially parallel with the longitudinal axis in the first and second tapered portions.

5. A fiber-reinforced medical balloon comprising:
a generally cylindrical central portion;
first and second generally conical portions connected to the generally cylindrical central portion along a central longitudinal axis extending from a first end of the balloon to a second end of the balloon;
a plurality of first fiber strands extending from the first end of the balloon to the second end of the balloon, each strand of the plurality of first fiber strands running substantially parallel to the central longitudinal axis through the generally cylindrical central portion;
at least one of the plurality of first fiber strands having at least one turn around on at least one of the first and second generally conical portions of the balloon; and
at least one second fiber strand extending radially around the generally cylindrical central portion, wherein the plurality of first fiber strands and the at least one second fiber strand are all part of a single continuous fiber.

6. The fiber-reinforced medical balloon of claim 5, wherein the strands of the plurality of first fiber strands are all part of a single continuous fiber.

7. The fiber-reinforced medical balloon of claim 6, wherein the single continuous fiber has a plurality of turn arounds on at least one of the first and second generally conical portions.

8. The fiber-reinforced medical balloon of claim 5, wherein each strand of the plurality of first fiber strands extends radially around at least a portion of at least one of the first and second generally conical portions, wherein each strand of the plurality of first fiber strands extends at an angle of approximately 35-90 degrees relative to the longitudinal axis of the balloon as the first fiber strands extend radially around at least a portion of the first and second generally conical portions.

9. The fiber-reinforced medical balloon of claim 5, wherein the at least one second fiber strand extends around the first and second conical portions at a lower pitch than a pitch of the at least one second fiber strand around the central portion.

10. The fiber-reinforced medical balloon of claim 5, wherein the at least one second strand extends over all of the strands of the plurality of first fiber strands.

11. The fiber-reinforced medical balloon of claim 5, wherein the at least one second strand extends over a first portion of the plurality of first fiber strands and under a second portion of the plurality of first fiber strands, wherein the first portion of the plurality of first fibers are on a first half of the balloon and the second portion of the plurality of first fibers are on a second half of the balloon.

12. A method of making a fiber-reinforced composite balloon having a generally cylindrical central portion and first and second tapered portions connected to the generally cylindrical central portion along a central longitudinal axis extending from the first end of the balloon to the second end of the balloon, the first and second tapered portions connected to the central portion together forming an interior compartment for receiving an inflation fluid, wherein the method comprises:
applying a single continuous fiber to the generally cylindrical central portion extending substantially parallel to the central longitudinal axis of the balloon; and
applying the single continuous fiber to at least one of the first and second tapered portions in such a manner as to have at least one turn around on at least one of the first and second tapered portions of the balloon.

13. The method of claim 12, comprising applying the single continuous fiber in such a manner as to have a plurality of turn arounds on at least one of the first and second tapered portions.

14. The method of claim 12, further comprising applying the single continuous fiber radially around the central portion of the balloon.

15. The method of claim 12, further comprising applying a second fiber radially around the generally cylindrical central portion of the balloon.

16. A method of making a fiber-reinforced composite balloon having a generally cylindrical central portion and first and second tapered portions connected to the generally cylindrical central portion along a central longitudinal axis extending from the first end of the balloon to the second end of the balloon, wherein the method comprises:
applying a single continuous fiber to the generally cylindrical central portion extending substantially parallel to the central longitudinal axis of the balloon;
applying the single continuous fiber to at least one of the first and second tapered portions in such a manner as to have at least one turn around on at least one of the first and second tapered portions of the balloon; and
applying the single continuous fiber radially around the central portion of the balloon.

* * * * *

UNITED STATES PATENT AND TRADEMARK OFFICE
CERTIFICATE OF CORRECTION

| | |
|---|---|
| PATENT NO. | : 12,059,534 B2 |
| APPLICATION NO. | : 17/723754 |
| DATED | : August 13, 2024 |
| INVENTOR(S) | : Tilson et al. |

It is certified that error appears in the above-identified patent and that said Letters Patent is hereby corrected as shown below:

In the Claims

Column 15, Claim 6, Line 22, please delete "the strands of".

Signed and Sealed this
Tenth Day of September, 2024

*Katherine Kelly Vidal*

Katherine Kelly Vidal
*Director of the United States Patent and Trademark Office*